United States Patent

Shartle

[11] Patent Number: 5,912,134
[45] Date of Patent: Jun. 15, 1999

[54] DISPOSABLE CARTRIDGE AND METHOD FOR AN ASSAY OF A BIOLOGICAL SAMPLE

[75] Inventor: Robert J. Shartle, Livermore, Calif.

[73] Assignee: Biometric Imaging, Inc., Mountain View, Calif.

[21] Appl. No.: 08/783,127

[22] Filed: Jan. 14, 1997

Related U.S. Application Data

[62] Division of application No. 08/300,360, Sep. 2, 1994, Pat. No. 5,627,041.

[51] Int. Cl.⁶ .......................... G01N 33/53; G01N 33/558
[52] U.S. Cl. ............................. 435/7.24; 422/50; 422/55; 422/58; 422/68.1; 422/72; 422/82.06; 422/82.07; 435/287.1; 435/287.2; 435/287.6; 435/288.4; 435/288.5; 435/288.7; 435/808; 435/810; 435/973; 436/45; 436/70; 436/164; 436/165; 436/172; 436/179; 436/514; 436/809
[58] Field of Search .................................. 422/50, 55, 58, 422/68.1, 72, 82.06, 82.07; 435/7.24, 287.1, 287.2, 287.6, 288.4, 288.5, 288.7, 808, 810, 973; 436/45, 70, 164, 165, 172, 179, 514, 536, 805, 809

[56] References Cited

U.S. PATENT DOCUMENTS

| | | |
|---|---|---|
| D. 366,938 | 2/1996 | Shartle et al. . |
| 3,799,742 | 3/1974 | Coleman . |
| 4,125,828 | 11/1978 | Resnick et al. . |
| 4,868,129 | 9/1989 | Gibbons et al. . |
| 4,946,795 | 8/1990 | Gibbons et al. . |
| 5,061,446 | 10/1991 | Guigan . |
| 5,077,017 | 12/1991 | Gorin et al. . |
| 5,173,193 | 12/1992 | Schembri ................................ 210/782 |
| 5,256,376 | 10/1993 | Callan et al. . |
| 5,338,427 | 8/1994 | Shartle et al. . |
| 5,472,603 | 12/1995 | Schembri ................................ 356/246 |

FOREIGN PATENT DOCUMENTS

WO 93/19827   10/1993   WIPO .

*Primary Examiner*—Christopher L. Chin

[57] ABSTRACT

A cartridge is provided to present a biological sample for analysis by an imaging instrument. The cartridge of the invention utilizes a series of channels, capillaries, reservoirs and stop junctions to precisely move a sample, reagent and diluent through the cartridge as a function of the sum of capillary, gravitational and low centrifugal forces. The operator applies a precise amount of sample to the cartridge; therefore, the cartridge fluidics need not meter the sample prior to dilution. A practical and cost effective cartridge and assay process is disclosed which overcomes many of the limitations of the prior art. Such a cartridge is especially useful with fixed volume assays which permit low centrifugal accelerations to move the fluids within the cartridge.

16 Claims, 9 Drawing Sheets

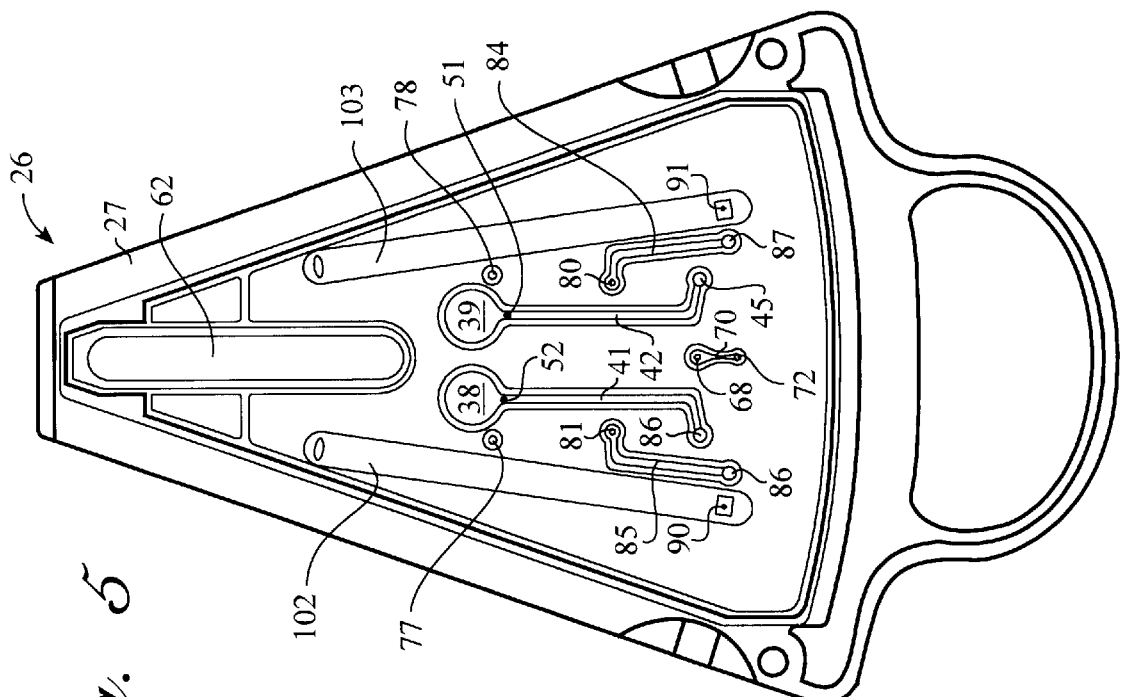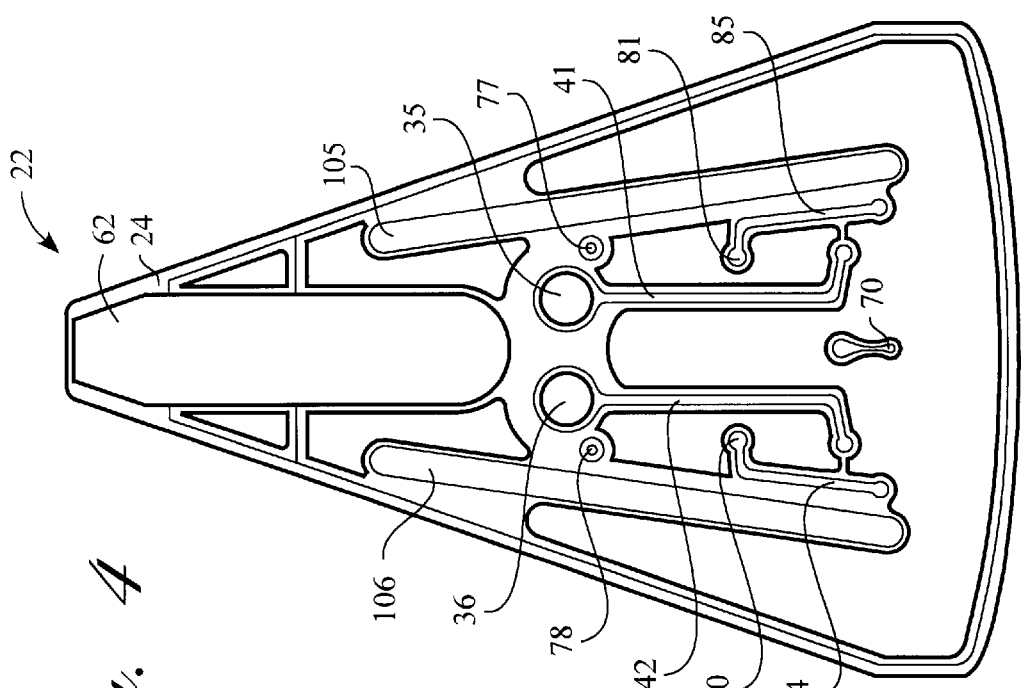

DISPOSABLE CARTRIDGE AND METHOD FOR AN ASSAY OF A BIOLOGICAL SAMPLE

This application is a divisional of U.S. Ser. No. 08/300,360 filed Sep. 2, 1994 entitled DISPOSABLE CARTRIDGE FOR AN ASSAY OF A BIOLOGICAL SAMPLE IN A SCAN CAPILLARY FOR IMMUNOFLUORESCENT INTERROGATION now U.S. Pat. No. 5,627,041.

BACKGROUND OF THE INVENTION

This invention relates generally to improvements in apparatus and methods for simultaneously analyzing a plurality of fluid samples to determine the concentration of one or more solid components contained within each sample. More specifically, the present invention relates to an assay cartridge and method for conducting an immunoassay using the assay cartridge to dilute a plurality of blood samples simultaneously and to present the diluted samples for analysis by an imaging instrument.

The recent proliferation of diagnostic tests for an increasing variety of clinically significant target components has created a demand for routine monitoring of these components in patient samples. For example, the blood concentration of T-lymphocytes expressing the CD4 or CD8 surface antigens is widely accepted as a reliable indicator of disease stage in individuals diagnosed with the human immunodeficiency virus (HIV). The need for a cost effective reliable method for routine analysis has led to the development of single-use assay cartridges.

In such a cartridge, a small volume of blood sample is applied to the cartridge by an operator of an analytical instrument. The cartridge is then inserted in the instrument which automatically performs the remaining assay steps. The quantity of reagents used is minimized and the potential for operator error or exposure to biohazardous materials is greatly reduced when such assay cartridges are used. Such cartridges are readily adapted for various assay methods, such as transporting and metering of the sample or reagent, dilution of the sample and presentation of the sample for analysis.

Numerous assays have been developed for identifying a variety of target components found in biological samples. In such assays, a biological sample, e.g. blood or urine, is reacted with a reagent which modifies the component to be detected. Examples of reagents commonly used include binding agents and ligands such as monoclonal antibodies, degradative agents such as protease, and labels such as fluorescent dyes, u.v. active and radioactive compounds. Frequently, the reagent is a monoclonal antibody bound to a fluorescent dye. An imaging instrument is used for quantitative and qualitative analysis of a mixture of the sample and reagent. Once the sample is mixed and incubated with the reagent, an aliquot of the mixture is then isolated and analyzed for the presence or absence of the target component. Immunoassays on blood samples where fluorescent tagged antibodies are used to bind to specific blood cells are examples of such assays.

For an aliquot of an assay sample to be representative of a biological sample as a whole, it is important that the target component be evenly distributed within the sample when analyzed. The assay process should not create an uneven distribution of the component within the sample. Some prior art cartridges and assays, however, subject the sample to large centrifugal forces which disrupt the distribution of the components within the sample. Similarly, larger target components in suspension in the sample, such as blood cells, are susceptible to undesirable settling due to gravity. It is desirable to configure the cartridge and the assay process to maintain proper target component distribution within the sample.

Most prior assay cartridges are configured to perform multiple analyses on a single sample. It is also desirable to simultaneously perform one or more assays on multiple samples. Simultaneous processing of multiple samples requires consideration of certain time constraints when processing the assay. For example, when the concentration of the target component is determined by fluorescence emissions, the signal detected by the imaging instrument frequently varies with the period of time that the sample is contacted with the reagent. Therefore, it is important that all the samples be assayed using the same or similar time conditions.

It is also frequently desirable and/or necessary to dilute the biological sample in order to accurately detect the amount of target component present. For example, it may be necessary to dilute concentrated biological samples so that a fluorescent signal from the sample and reagent mixture falls within an easily detectable or linear range. However, the degree of dilution needed varies depending on the initial concentration of the component within the sample. It is, therefore, important to be able to accurately dilute the samples being analyzed.

To achieve sample dilution, prior art cartridges frequently have utilized complex designs which are costly and difficult to manufacture. The complexity found in the cartridges is in part due to the metering of the sample within the cartridge. If the sample metering is performed using small hand-held pipets, then the configuration of the cartridge may be simplified. Thus, it is desirable to eliminate the metering aspects of the cartridge so as to simplify the cartridge design. This also provides for variable dilution ratios.

When the cartridge comprises a self-contained dilution apparatus, various configurations of capillaries, conduits, chambers, reservoirs, application wells and stop junctions are used to move the sample, reagent and/or diluent within the cartridge. Prior art cartridges use capillary, gravitational and/or centrifugal forces to move the fluids within the cartridge. It has been disclosed to use capillary backpressure to create a "stop junction" which stops the flow of the fluids under certain conditions, while allowing flow under other conditions. Such stop junctions or stop flow capillaries act as valves without moving parts. The stop junctions are opened or "broken" by changing the pressure, force or acceleration applied to the fluid in the capillary forming the stop junction.

Prior art cartridges using a capillary to form a stop junction did not contemplate using low centrifugal accelerations to move the fluid past the stop junction. Prior art cartridges use high rotational speed or changes in fluid level in a reservoir to overcome the stop junction. In certain cartridge designs, variable fluid levels may be unavailable or undesirable. Similarly, high rotational speeds which may be desirable for separating plasma or similar components, can be detrimental to certain components within a sample. Thus, it is desirable to configure an assay or dilution cartridge which would move the sample, diluent and/or reagent by means of low centrifugal forces.

Various assay cartridges having dilution fluidics and various assay cartridges configured for centrifugal acceleration have been known for a number of years, and by way of example, several forms of such devices can be found in U.S. Pat. Nos. 4,728,500; 4,756,884; 4,946,795; 5,061,381; 5,122,284; 5,173,193; 5,186,844; 5,230,866 and 5,300,779.

One system which incorporates the optics capable of using an assay cartridge is disclosed in co-pending U.S. patent application Ser. No. 08/236,342 entitled "Apparatus and Method for Volumetric Capillary Cytometry" invented by Thomas M. Baer, Louis J. Dietz, Robert S. Dubrow, Paul G. Hayter, Michael Hodges, Bala S. Manian and Robert J. Shartle, owned by the same assignee as this application and incorporated herein by reference. Similarly, a method and apparatus for gathering and analyzing data available from an assay cartridge is described in co-pending U.S. patent application Ser. No. 08/236,645 entitled "Method and Apparatus for Cell Counting and Cell Classification" invented by Ning L. Sitzo and Louis J. Dietz, also owned by the same assignee as this application and also incorporated herein by reference.

Hence, those concerned with the development and use of assay cartridges for the movement and dilution of fluid samples have long recognized the need for improved fluidic circuits. With the introduction of imaging instruments which use a diluted whole blood sample in a fixed volume, such as those described in the applications incorporated above, a need is now recocognized for systems which move the sample without subjecting the sample and the cartridge to high centrifugal accelerations. The present invention solves each of these needs.

SUMMARY OF THE INVENTION

Briefly, and in general terms, the present invention provides a new and improved cartridge or cassette for use in an imaging instrument for analyzing a sample of biological fluids, such as human whole blood. The cartridge includes multiple channels for parallel processing, as well as the necessary reagents, such as diluent and fluorescent markers. Multiple wells are provided for receiving multiple samples of the biological fluid under study. A system of interconnected conduits control the movement of the sample and diluent into one or more mixing chambers and then into one or more scan capillaries for analysis.

By way of example and not necessarily by way of limitation, when the fluid to be sampled is blood, a first reagent having antibodies tagged with fluorescent dyes is placed in one or more application wells. Upon application of a precise volume of blood sample into each application well, the first reagent is combined with the samples. The cartridge is reciprocated to thoroughly blend the sample and reagent. A fluid conduit extends from each application well to a first reduced cross-sectional size capillary forming a first stop junction. Without the application of additional force, the mixed sample will remain in the application wells and conduits and will not proceed through the first stop junction.

After the blood sample or other biological fluid has combined with the first reagent, the cartridge is subjected to centrifugal forces to move the sample past the first stop junction and into a mixing chamber. The configuration of the application wells and conduits is selected so that when a centrifugal acceleration is applied by spinning the cartridge on a platter of the imaging instrument, a pressure in the fluid at the stop junction causes the sample to flow through the conduits into the mixing chambers. Once the mixed sample has exited the application well, the conduits are configured to prevent the sample from leaving the cartridge. The sample and reagent are allowed to incubate in the mixing chamber for a preset period of time. A vial that also resides in the cartridge is then opened to allow a diluent to flow into a reservoir and a connected conduit. The distal end of this conduit is coupled to a second stop junction having a size small enough so that the diluent will not proceed through the second stop junction without the application of additional force.

After incubation of the blood sample and reagent, the cartridge is spun again. The centrifugal force on the fluids in the cartridge breaks the second stop junction, and causes the diluent to flow from the reservoir into the mixing chamber. The mixing chamber has a precisely determined size so that only a predetermined volume of fluids can be received. An exit conduit from each mixing chamber is provided with an exit stop junction to maintain the sample and diluent in the mixing chamber. In addition, each mixing chamber includes a mixing ball to ensure thorough mixing of the sample and diluent, and to minimize settling and separation of the particulates or constituents of the sample.

Once the incubated sample and the diluent have filled the mixing chamber, the cartridge is positioned proximate a magnet which is moved linearly to move the mixing ball in a desired mixing motion. The sample and diluent are then mixed in the chamber for a predetermined period of time. Upon the expiration of that time, the cartridge is spun at a higher RPM to subject the cartridge to a higher centrifugal acceleration which causes the mixed fluid in the chamber to leave the chamber through the exit stop junction.

Also formed into the cartridge is a precise scan capillary for use by the imaging equipment in the analysis of the biological fluid. Upon the application of the aforementioned higher centrifugal acceleration, a precise quantity of the mixed sample and diluent flow from the mixing chamber into the scan capillary. Once the scan capillary is filled, the diluted sample is available to the analytical equipment for imaging or other analysis. The construction and use of materials in the cartridge of the present invention results in a inexpensive disposable apparatus. Thus, after the final analysis of the biological fluids by the imaging equipment, the cartridge may be discarded.

Multiple scan capillaries may be included in the cartridge to enable parallel processing of multiple samples of biological fluids. Different diluents and/or reagents may be included in the cartridge to provide for the processing of different assays on the same patient sample. The sizes of the internal conduits and capillaries are chosen in dependence on the characteristics of the fluids to be processed. As described above, stop junctions are configured into the cartridge such that fluid will not pass without the addition of external forces, such as from a centrifugal acceleration. The stop junction configuration provides a controlled environment for fluid movement resulting in increased accuracy.

One of the unique and novel features of the cartridge of the present invention is the incorporation of a series of capillaries, conduits and reservoirs to form stop junctions which control the flow of the sample and diluent through the cartridge. The present invention includes the configuration of a stop junction whose capillary backpressure is overcome by the application of a centrifugal acceleration caused by the relatively slow rotation of the cartridge within the imaging instrument. The cross-sectional area, radial position and fluid pressure of each capillary, reservoir and stop junction are precisely selected to induce or prohibit flow through the stop junctions during the steps of the assay process. Moreover, a series of selected centrifugal accelerations are applied to the cartridge to move the fluids in a desired fashion.

The cartridge of the present invention also includes mounting and handling features. Presently, two guide rails on each side of the cartridge exists and include locking recesses for receiving external locking mechanisms to hold the cartridge in a fixed position during the imaging processing. A thumb grip is attached to the distal end of the cartridge for use in inserting and removing the cassette from the imaging instrument. The cartridge is preferably substantially triangular in shape for use of multiple cartridges in an instrument having a round turntable or platter for applying the centrifugal accelerations. Because a plastic body for the cartridge is used, ultrasonic welding is a process available for final assembly of the cartridge.

Thus, the new and improved assay cartridge of the present invention for the movement and dilution of fluid samples includes improved fluidics circuits. Such improved fluidics circuits are especially advantageous for use with a diluted whole blood sample in a fixed volume, such as those described in the applications incorporated above. The improved fluidics circuits move the sample without subjecting the sample, the instrument or the cartridge to high centrifugal accelerations. Moreover, the ability to configure cartridges which have stop junctions which permit fluid flow upon the application of low centrifugal accelerations opens the avenues for new uses of such assay cartridges.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIG. 4 is a bottom plan view of the top plate of FIG. 3.

FIG. 5 is a top plan view of the middle plate of the assay cartridge of FIG. 2.

DESCRIPTION OF THE PREFERRED EMBODIMENTS

As shown in the exemplary drawings, the present invention is embodied in a cartridge or cassette used for processing an assay for qualitative and quantitative analysis of target components in a biological sample. Whereas prior art cartridges merely employ static fluid control or subject the cartridge to high rotational speeds, the present invention avoids process steps which could disrupt the distribution of target components within the sample. Similarly, the present invention avoids the complexity of the fluidics of prior art cartridges caused by the incorporation of a metering step.

Figure 1:
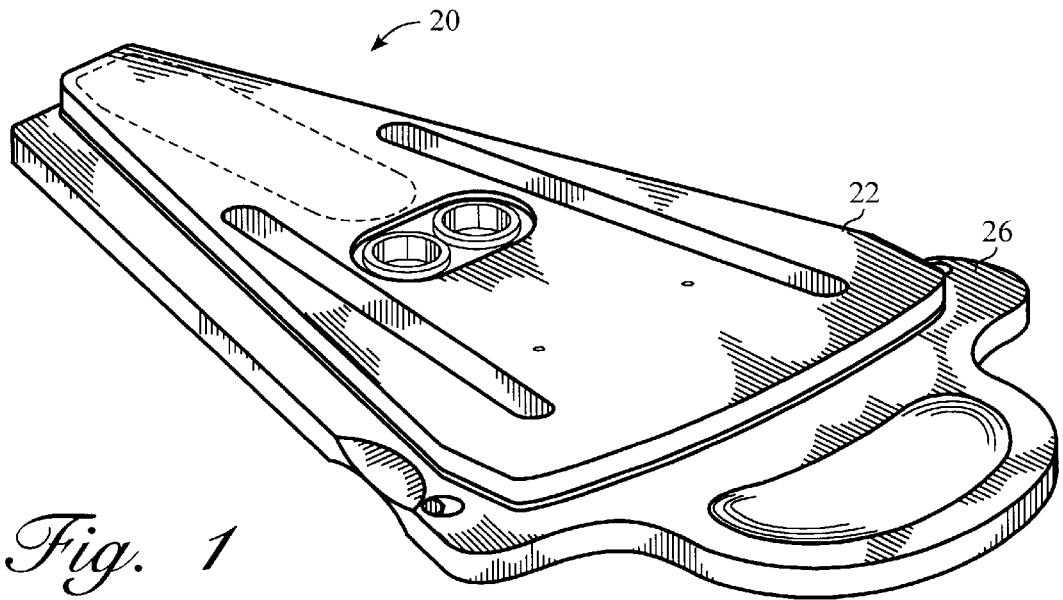
FIG. 1 is a perspective view of an assembled assay cartridge constructed in accordance with the invention.
Figure 2:
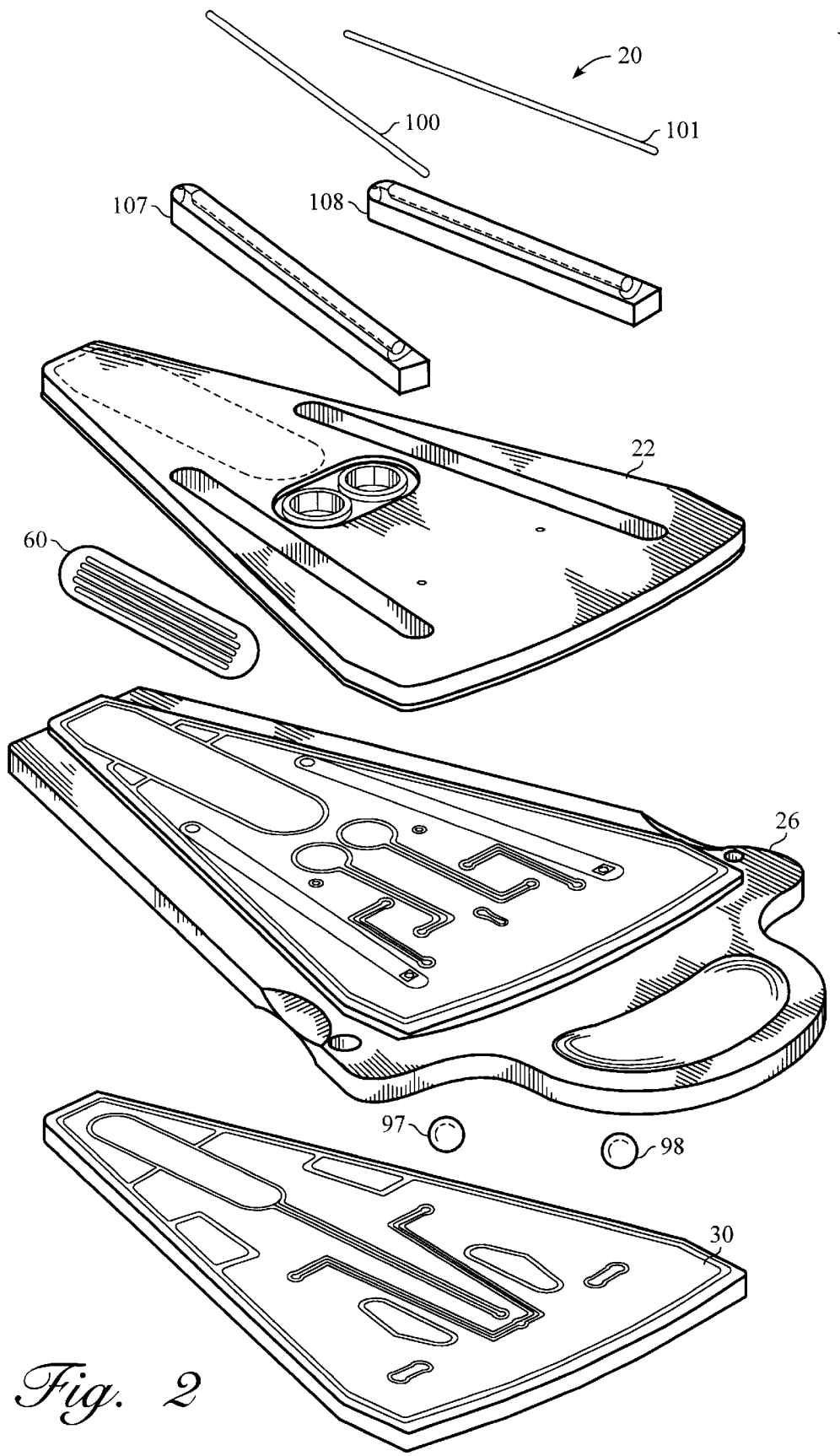
FIG. 2 is an exploded perspective view of the assay cartridge of FIG. 1.

In accordance with the present invention and as shown in FIGS. 1 and 2, a cartridge 20 is provided to present a biological sample for analysis by an imaging instrument. The cartridge of the present invention uses a series of channels, capillaries, reservoirs and stop junctions to precisely move a sample, reagent and diluent through the cartridge as a function of the sum of capillary, gravitational and low centrifugal forces. Since a precise amount of sample is applied to the cartridge, there is no need to meter the sample within the cartridge fluidics. Thus, a practical and cost effective cartridge and assay process is provided which overcomes many of the limitations of the prior art. Such a cartridge is especially useful with fixed volume assays.

Referring now more particularly to FIG. 2, the cartridge 20 comprises three molded plates 22, 26 and 30, preferably made of a plastic or the like, such as acrylonitrile butadiene styrene (ABS), polystyrene or polymethyl methacrylate. ABS suitable for manufacture of a cartridge incorporating the present invention may be purchased from BASF Corp. of Wyandotte, Mich. under the trademark "TERLUX 2802 TR." The ABS plates are fused together, preferably by ultrasonic welding, as shown in FIG. 1.

Figure 13A:
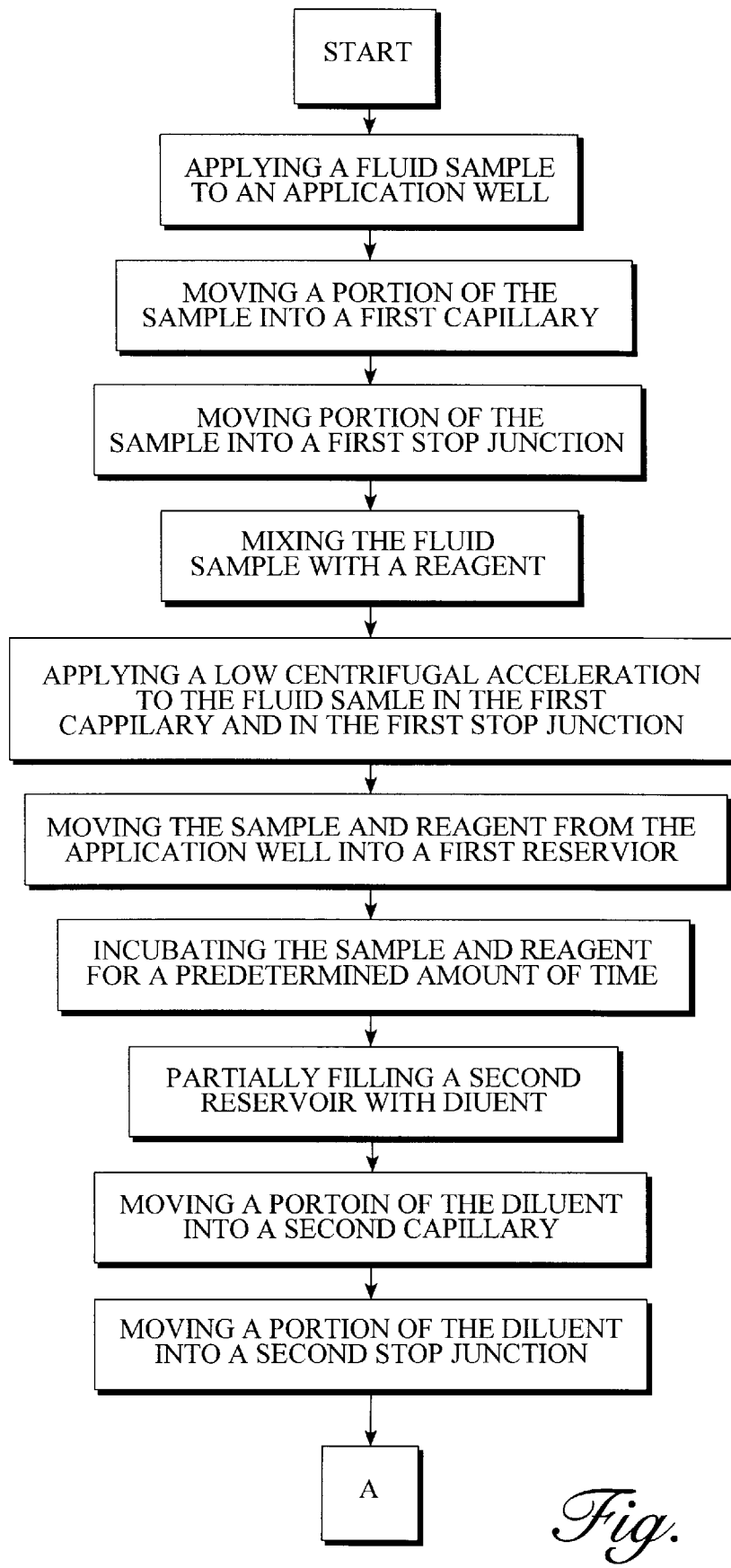
FIG. 13 is a process flow diagram of the steps taken in the dilution process utilizing a cartridge in accordance with the invention.
Figure 13B:
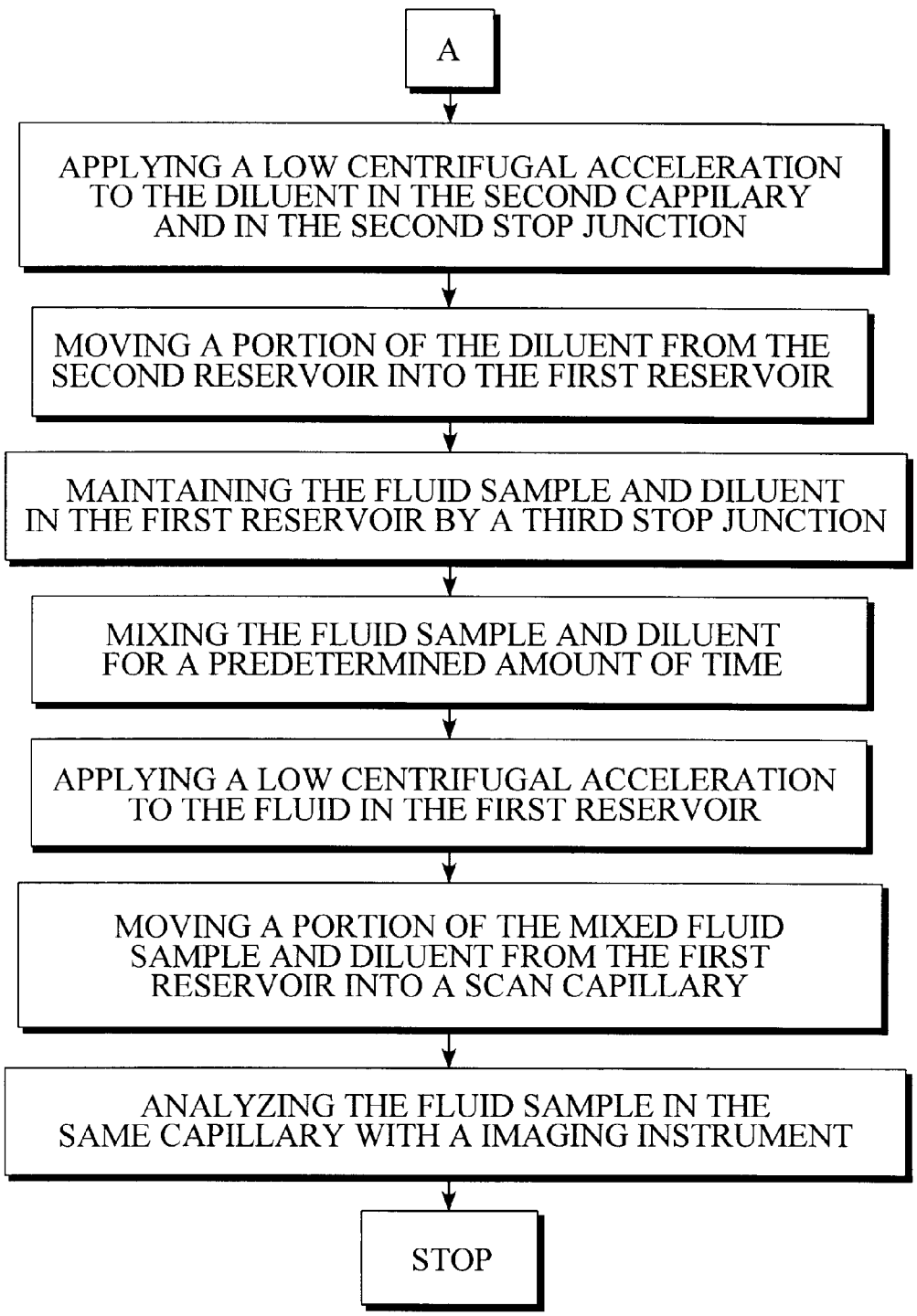

As shown in more detail in FIGS. 3–11, a top plate 22 has a top face 23 and a bottom face 24. A middle plate 26 has a top face 27 and a bottom face 28. A bottom plate 30 has a top face 31 and a bottom face 32. The cartridge plates are further configured with several wells, reservoirs, chambers, channels, capillaries and stop junctions for moving fluid flow through a combination of gravitational, capillary and centrifugal forces. The process for movement of the fluid through the cartridge is described further herein, as depicted in FIG. 13.

Figure 3:
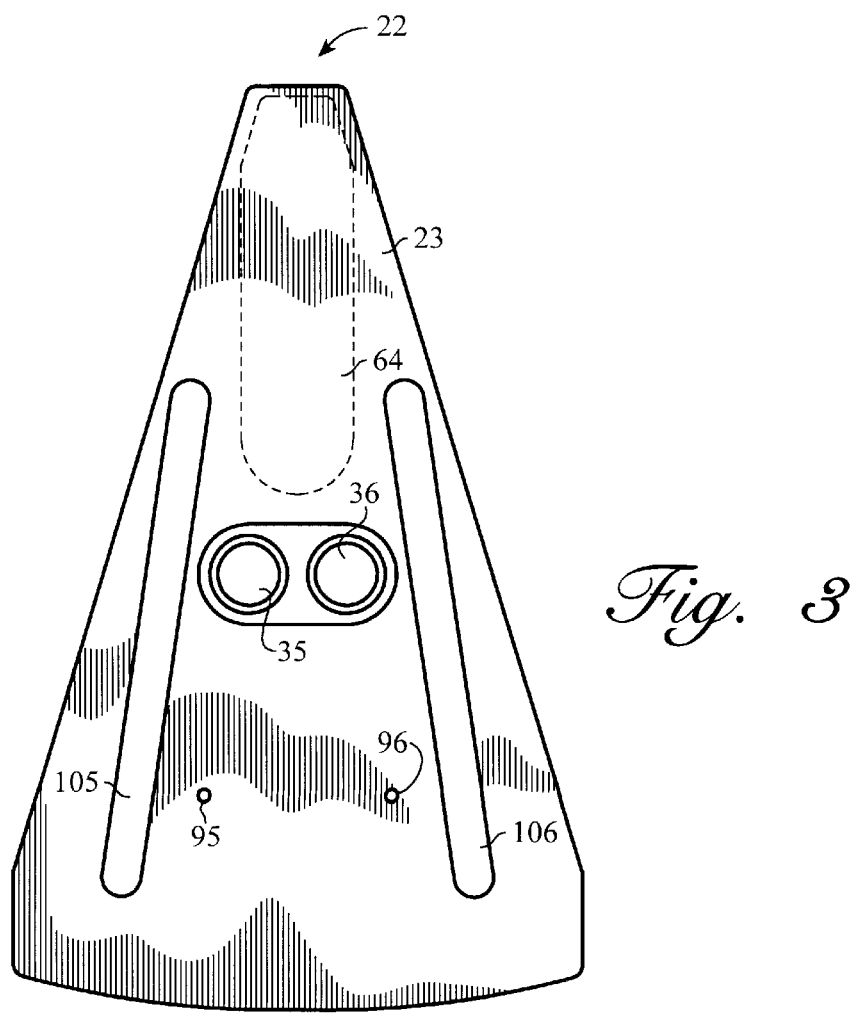
FIG. 3 is a top plan view of the top plate of the assay cartridge of FIG. 2.

To start an assay, an operator of an imaging instrument (not shown) used for processing the cartridge 20 applies a known amount of fluid sample into each of a pair of application wells 35 and 36, as best observed in FIGS. 3–5. Such application wells may be circular in cross section and cylindrical in overall shape; however, other configurations may be used. For an assay starting with whole blood, one hundred microliters of whole blood is applied to each of the application wells. Assays may be configured with more or less than one hundred microliters of sample placed in the application well, so long as the exact amount of sample is predetermined. Whereas the rest of the dilution process operates in a fixed volume, the ability to vary the sample volume provides for a variable dilution factor such that the operator may apply a variable, but predetermined, volume of the whole blood sample.

The application wells 35 and 36 are configured with bottom surfaces 38 and 39 molded in the top face 27 of the middle plate 26. During the assembly of the cartridge 20, a fixed amount of a reagent is dispensed onto the bottom surfaces of the application wells. The reagent for a CD4/CD8 assay typically is a sucrose solution which contains one or more antibodies tagged with a fluorescent dye. A very small drop, e.g., ten microliters, of the sucrose solution is placed in each application well and then passed though a drying tunnel (not shown) in the manufacturing process. The result is a very thin sugary film in the bottom of the two wells, forming a matrix which readily dissolves in an aqueous solution, such as blood.

When the operator of an imaging instrument places the blood samples into the application wells 35 and 36, the blood immediately begins to dissolve the antibodies contained in the reagent. For a CD4/CD8 assay, the first well contains CD3 and CD4 antibodies, and the second application well contains CD3 and CD8 antibodies. Thus, there are two different antibody mixtures in each of the application wells. The processing or imaging instrument is configured to determine which well is used for which assay, for example, by designating the left application well for CD4 and the right application well for CD8. Thus, the user can put blood from the same patient in each of the two wells and the imaging instrument determines which well contains each assay.

Figure 9:
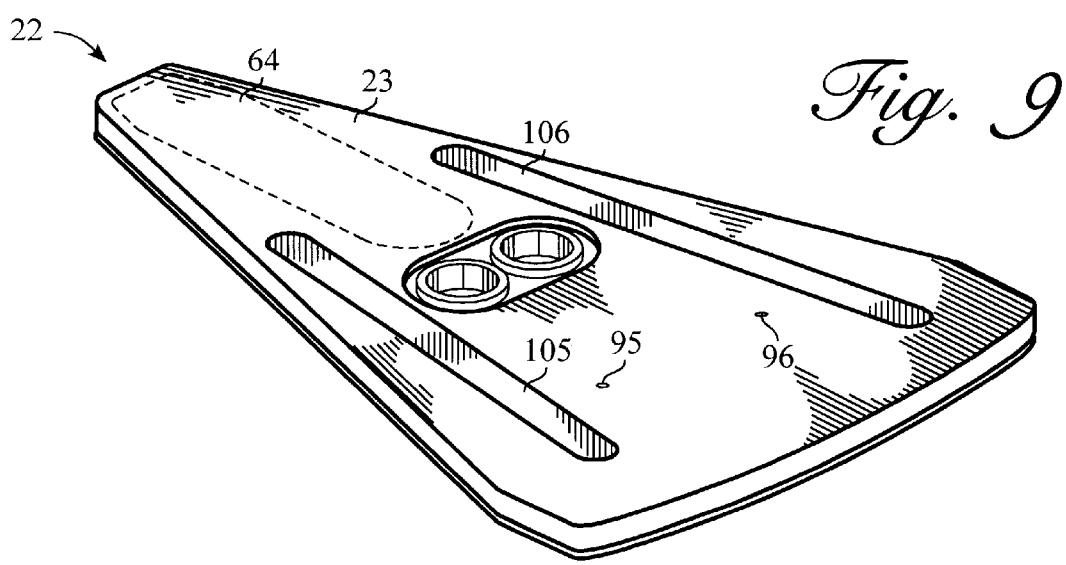
FIG. 9 is a top perspective view of the top plate of FIG. 3.
Figure 10:
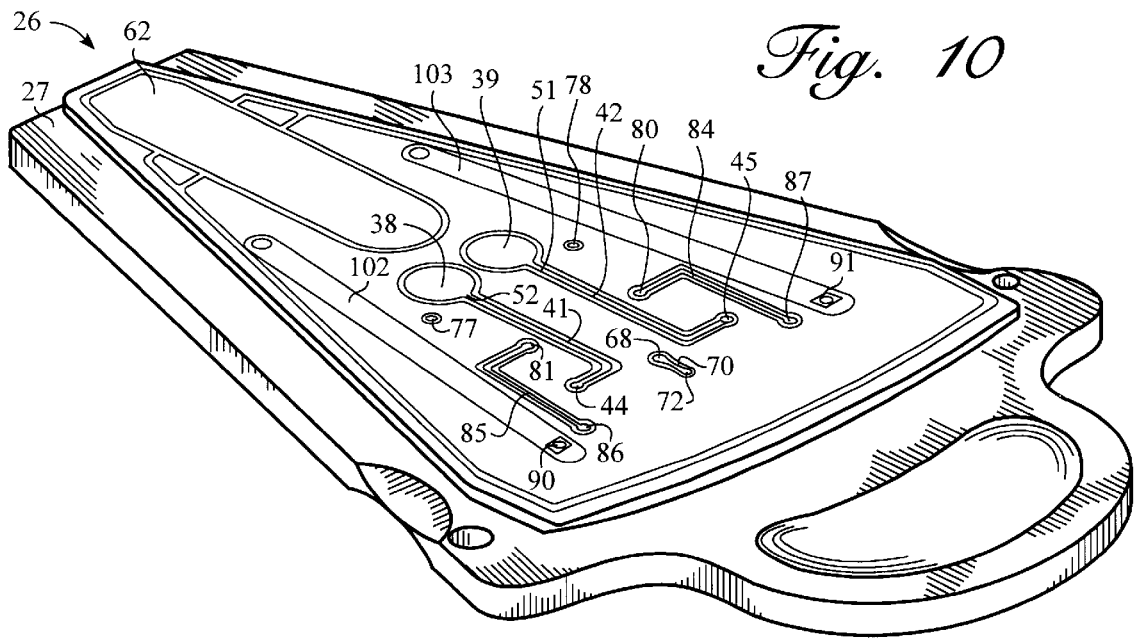
FIG. 10 is a top perspective view of the middle plate of FIG. 5.

As shown in FIGS. 4, 5 and 9, the application wells 35 and 36 are in fluid communication with the mixing chamber inlet capillaries 41 and 42. Such mixing chambers may have a cross section configured as a pentagon in shape to enhance the mixing properties of the chamber; however, other shapes of the mixing chambers may be used. When blood is added to each application well, each inlet capillary fills due to the combination of capillary and gravitational forces. The capillaries fill all the way to a pair of mixing chamber inlet stop junctions 44 and 45, shown in FIGS. 3 and 4. The wetability and capillary action of the cartridge material, such as ABS, may be enhanced by plasma etching or similar techniques.

The mixing chamber inlet stop junctions 44 and 45 are small circular capillaries which pass through the middle plate 26 which connect the inlet capillaries 41 and 42 to the mixing chambers 48 and 49. Typical diameters for the inlet stop junctions range from 0.5 mm to 1.5 mm, and are preferably 1.1 mm. The stop junctions or stop flow capillaries need not necessarily be configured with circular cross sections, and are best manufactured in at least two planes in the cartridge, i.e., on two surfaces or levels of the cartridge plates 22, 26 and 30.

As the sample fluid flows though the mixing chamber inlet capillaries 41 and 42, the fluid also fills two wash stop junctions 51 and 52, due to the combination of capillary and gravitational forces caused by the sample in the application wells 35 and 36. The wash stop junctions fill with sample, but they do not allow fluid to flow beyond each stop junction. The wash stop junctions are positioned so that in later steps of the assay process the diluent will flow through the stop junctions and wash out the sample that remains in the inlet capillaries. Precautions must also be taken in later steps of the assay to ensure that any blood cells which settle in the wash stop junctions are dissolved or moved through the wash stop junctions.

Each stop junction is strong enough to withstand the static pressure associated with the gravitational or head pressure created by the blood in each application well 35 and 36. Preferably, each application well is about one-third of the way filled at this point in the dilution process, creating a slight gravitational head pressure. The application wells are configured such that the head pressure is not enough to break either the mixing chamber inlet stop junctions 44 and 45 or the wash stop junctions 51 and 52. It is important that the four stop junctions do not break. Therefore, the stop junctions are sized with a small enough cross-sectional area so that they will withstand the head pressure caused by the sample in the application wells. Typical diameters for circular wash stop junctions range from 0.375 mm to 0.75 mm, and are preferably 0.5 mm in diameter.

At this point in the method, approximately eighty-five of the original one-hundred microliters of the blood sample is still in the application wells 35 and 36. About fifteen microliters of the sample is in the mixing chamber inlet capillaries 41 and 42. The dried reagent containing antibody deposited in the application wells has begun to dissolve into the blood. To provide increased convection and diffusion based mixing and dissolving of the reagents, the cartridge is reciprocated back and forth by the imaging instrument.

As shown in FIGS. 3, 4 and 9, the top plate 22 of the cartridge 20 is designed and configured it so that the blood sample will stay in each application well 35 and 36 and not spill out of the well. The application well is configured with a maximum volume so that the well is only about one-third of the way filled after application of the sample. Further, the well has sharp edges to retain the sample and reagent within the well when the cartridge is reciprocated. Thus, the application well configuration provides for good mixing, such that within about three minutes of reciprocation the antibody is homogeneously dissolved in the blood sample.

The portion of the blood sample that is in the inlet capillaries 41 and 42, however, has had little or no exposure to the antibody containing reagent. To expose the blood cells in the capillaries to antibody, the remaining sample containing reagent from the application wells 35 and 36 must be transferred into the mixing chambers 48 and 49. Such a transfer is especially important when multiple assays are being performed on multiple cartridges within the same imaging instrument and the incubation of each sample and reagent is occurring simultaneously. If the portion of the sample from each inlet capillary is not transferred to the mixing chamber, then there will be incomplete incubation of the sample, which may introduce error into the analysis of the imaging instrument.

At this point in the assay process, seventy of the eighty-five microliters of sample from the application wells 35 and 36 and fifteen microliters of sample from the inlet capillaries 41 and 42 are transferred to the mixing chambers 48 and 49 by the sum of the capillary, gravitational and centrifugal forces. Fifteen microliters of combined sample and reagent remain in each inlet capillary. Spinning the cartridge 20 avoids directly pressurizing the application well, avoids the use of pumps and any other kind of physical contact with the cartridge. Spinning the cartridge provides a centrifugal acceleration of the fluids in the inlet capillary, thereby creating the primary force which overcomes the capillary backpressure at the inlet stop junctions 44 and 45. Moreover, by spinning multiple cartridges on a single platter 110 of an imaging instrument, see FIG. 12, the transfer of the sample to the mixing chambers can be accomplished for a plurality of cartridges at the same time.

The transfer of the sample into the mixing chambers 48 an 49 is effected by sizing the cross-sectional area and radial position of the inlet stop junctions 44 and 45, as discussed further herein. The preferred diameter of circular inlet stop junctions is approximately 1.1 mm. Consequently, when the cartridge 20 is spun at a rotational speed to create a low centrifugal acceleration on the fluid column leading to the inlet stop junctions, e.g., eighty revolutions per minute (RPM), a pressure is provided in the mixing chamber inlet capillaries 41 and 42 which overcomes the backpressure at the inlet stop junctions. The capillary back pressure may be increased by treating the ABS cartridge material with an oxygen plasma.

Upon spinning of the cartridge 20, sample with reagent flows from the application wells 35 and 36 into the mixing chambers 48 and 49. Where the original sample applied to each application well contained one hundred microliters of whole blood, each mixing chamber is filled with approximately eighty-five microliters of antibody containing blood, since fifteen microliters remain in the mixing chamber inlet capillaries 41 and 42. In addition, the inlet capillaries are sized such that the capillary forces therein are strong enough so that the inlet capillaries remain filled with sample at the maximum cartridge spin speed. Thus, each mixing chamber inlet capillary remains filled with blood, maintaining fluid contact with the mixing chamber inlet stop junctions 44 and 45. Likewise, the sample in the inlet capillaries maintains fluid contact with the wash stop junctions 51 and 52, which is critical to the functioning of the cartridge.

Having moved to the mixing chambers 48 and 49, the portion of the blood sample that was in each inlet capillary 41 and 42 has mixed with the blood that previously was in each application well 35 and 36, which is now empty of sample. The blood sample has also mixed with the reagent containing the fluorescent antibody and the mixture incubates and reacts in the mixing chamber. From the original one hundred microliter sample, about eighty-five microliters is now in each mixing chamber. About fifteen microliters of the sample is from the inlet capillary and probably did not contain much antibody. The other seventy microliters is from the application well, and has sufficient antibody for the entire sample.

Keeping the volume of the mixing chamber inlet capillaries 41 and 42 small is critical to minimize the variation of volume of the sample not having reagent when entering the mixing chambers 48 and 49. Minimizing the capillary volume also turns out to be important in the next process steps where the remaining sample in each inlet capillary is washed into the mixing chambers. Also, in optimizing the assay, excess amounts of antibody are used so that there is a wide range of concentrations that will provide the correct degree of sample labeling.

At this point in the dilution process, the blood sample and reagent have been transferred into the mixing chambers 48 and 49 for incubation. It is desired for a CD4/CD8 assay that the antibodies bind to as many of the antigen sites as possible. Thus, the sample and reagent should be allowed to react or incubate for a sufficient period to drive the reaction to completion, e.g., twenty minutes. During the incubation period, the imaging instrument may be configured to stop or to continue to spin the cartridge 20. It is preferable to stop spinning the cartridge to minimize cell migration, to reduce instrument noise and wear, and to conduct quality control diagnostics. For example, optical scan ports 95 and 96, shown in FIGS. 3 and 9, are provided to allow the imaging instrument to detect the presence of sample in the mixing chambers 48 and 49.

After the incubation is complete, the next step is to dilute the sample and then transfer a portion of the sample and diluent mixture for scanning by the imaging instrument. One reason for diluting is to lower the fluorescent background noise caused by excess antibody. To minimize the assay incubation period, and to drive the reaction to completion, a large amount of excess antibodies are used in the reagent. After the blood cells in the sample have been labeled, most of the antibodies remain suspended in the liquid phase of the sample, i.e., the plasma. Another reason to dilute is to reduce the density of red blood cells in the sample. Such cells are relatively large and interfere with the capability of the imaging instrument to process the target cells' fluorescent signals.

When scanning an undiluted mixture of antibody containing cells and plasma, the plasma may have an undesirable fluorescent level relative to the tagged cells. Although the fluorescent tagged cells may be distinguishable from the background fluorescence, the amount of noise caused by the excess antibody may be unsuitable for accurate analysis. Thus, to optimize the precision and accuracy of the assay, the sample mixture is diluted by factor 2.75:1 to bring the background noise down to a more acceptable level.

As shown in FIG. 2, an ampule 60 made of glass or similarly easily crushable material is disposed or mounted in the cartridge 20. The glass ampule is inserted in a retaining chamber or diluent reservoir 62 during the assembly of the cartridge. In the preferred embodiment, the cylindrical glass ampule contains about one thousand microliters of diluent, such as Dulbecco's phosphate buffered saline (PBS) available from Curtin Mathison Scientific of Houston, Tex. (CMS) mixed with bovine serum albumin (BSA) also available from CMS and crystalline sodium azide available from Sigma Corp. of St. Louis, Mo. The ampules are made of glass and are designed and manufactured to crush very regularly. The preferred ampule is elliptical having a diameter of 8.0 mm and a length of about 38.6 mm. This particular form of the ampule is available from James Alexander Corp. of Blairstown, N.J.

To dilute the sample mixture, the cartridge 20 is struck with a shaft or similar element of the imaging instrument (not shown) to break the glass ampule 60 and release the diluent into the diluent reservoir 62. A top wall 64 (FIG. 9) of the diluent reservoir is deflected downward by the shaft sufficiently so that the ampule is crushed. If the imaging instrument strikes the cartridges one at a time when processing a plurality of sample cartridges, the sample mixtures may not be diluted exactly at the same time, which is not optimum. For the CD4/CD8 assay as described herein, sequential crushing of the glass ampules is adequate.

Figure 7:
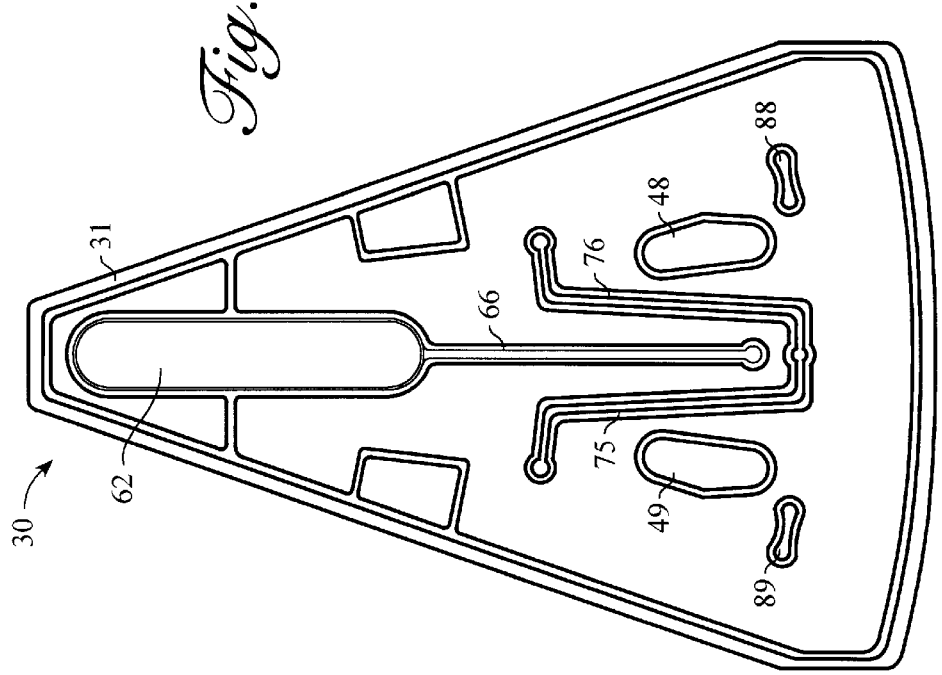
FIG. 7 is a top plan view of the bottom plate of the assay cartridge of FIG. 2.
Figure 6:
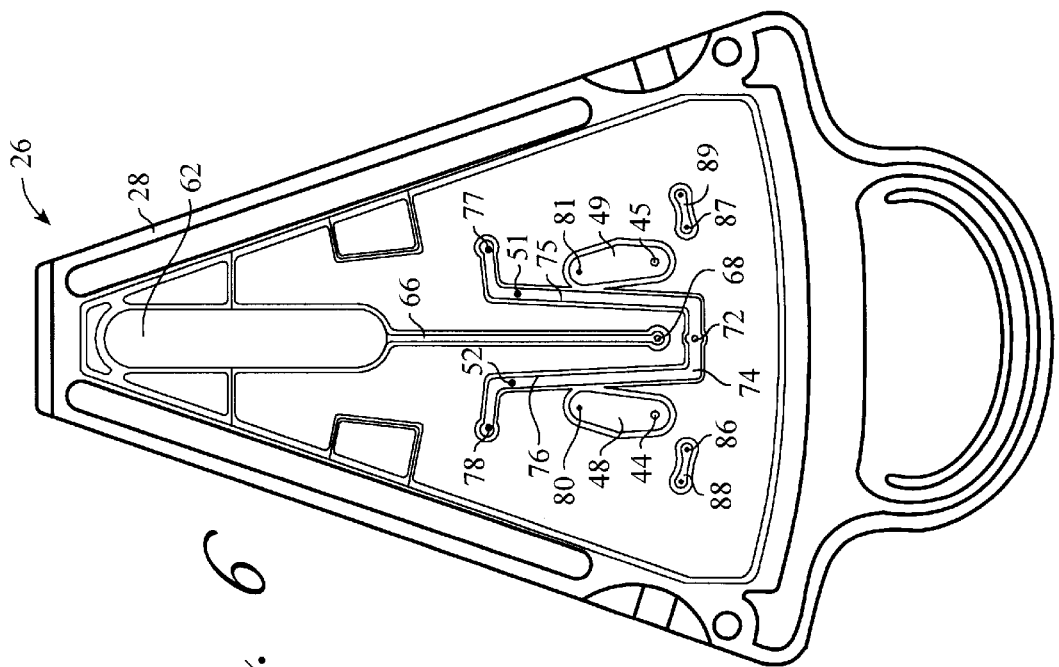
FIG. 6 is a bottom plan view of the middle plate of FIG. 5.
Figure 8:
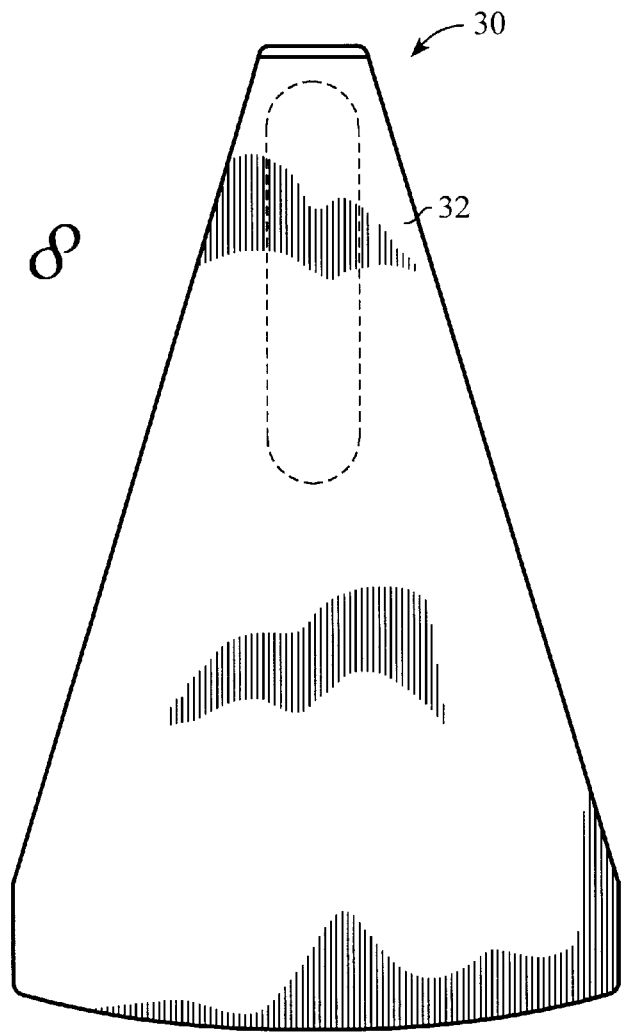
FIG. 8 is a bottom plan view of the bottom plate of FIG. 7.
Figure 11:
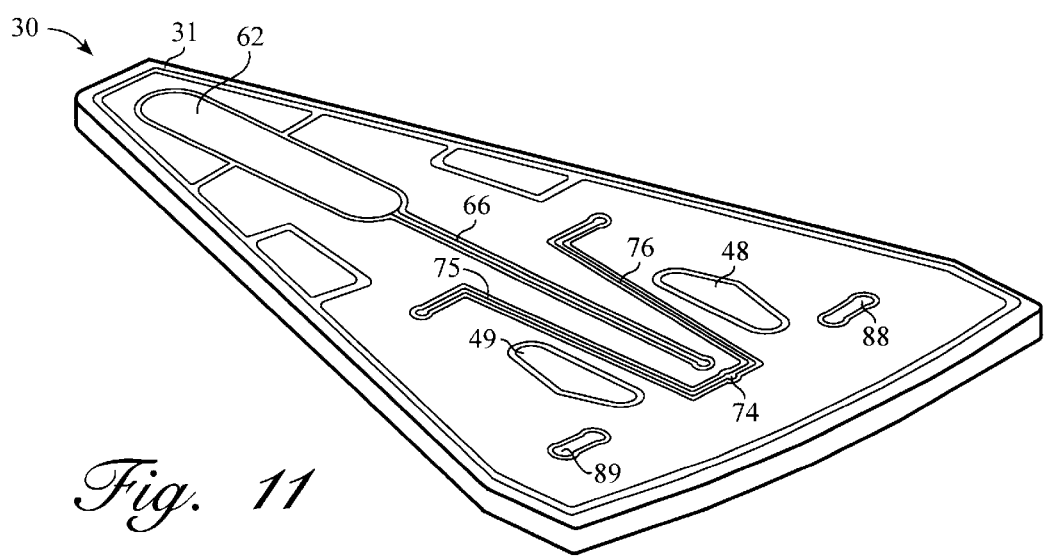
FIG. 11 is a top perspective view of the bottom plate of FIG. 7.

As shown in FIGS. 6, 7 and 11, a diluent exit capillary 66 is configured in the middle and bottom plates 26 and 30 of the cartridge 20 to draw diluent from the diluent reservoir 62. The diluent exit capillary is preferably circular in cross section. When the glass ampule 60 is broken by the imaging instrument, diluent fills the exit capillary by a combination of gravity and capillary forces. The diluent capillary fills to its distal end where a diluent exit stop junction 68 is configured in the middle plate 26, FIGS. 5 and 6. Since there is insufficient head pressure generated by the level of diluent in the reservoir to overcome the capillary strength of the diluent stop junction, the stop junction prevents the diluent from flowing further into the cartridge. Consequently, the imaging instrument may sequentially break the glass ampules of other cartridges without diluent mixing with the samples. This provides for multiple processing of cartridges wherein the dilution of the sample in the mixing chambers occur simultaneously.

The same diluent containing glass ampule 60 is used to dilute the samples from both application wells 35 and 36 for each cartridge 20. Alternatively, a separate glass ampule or diluent source could be provided for each application well and sample. Similarly, the diluent could be administered to the application well or similar inlet port by the imaging instrument or user. The construction of the cartridge shown in FIG. 2 provides a single glass ampule which decreases the size and cost of the cartridge, while eliminating a diluent source from the imaging instrument.

The next step in the dilution process is to move the diluent into the mixing chambers 48 and 49. As shown in FIGS. 5 and 6, a plurality of capillaries and stop junctions are used to wash the remaining sample from each mixing chamber inlet capillary 41 and 42 into each mixing chamber. The capillary in the diluent exit stop junction 68 is sized so that diluent will traverse the stop junction at a spin speed slightly lower than eighty RPM. The cartridge spin profile is preferably such that the spin speed is ramped up to eighty RPM in ten seconds, held at eighty RPM for fifty seconds and ramped down to zero RPM in five seconds. Such a spin profile could also be used for the steps of breaking the mixing chamber inlet stop junctions 44 and 45 described heretofore.

When the fluid pressure caused by the spinning cartridge 20 overcomes the diluent exit stop junction 68, diluent enters diluent cross channel 70 configured in the bottom face 24 of top plate 22 and the top face 27 of middle plate 26, FIGS. 4 and 5. The fluid pressure forces the diluent through the cross channel and into a diluent cross channel exit capillary 72 configured in the middle plate, FIGS. 5 and 6. The diluent continues to flow into a diluent connecting channel 74 configured in the bottom face 28 of the middle plate and the top face 31 of the bottom plate 30, FIGS. 6 and 7. The diluent connecting channel includes a first connecting arm 75 and a second connecting arm 76 each having a vent 77 and 78 for purging air as the fluid fills the capillary.

The diluent connecting channel provides an interface to the mixing chamber inlet capillaries 41 and 42. The first connecting arm 75 is located in the bottom of the middle plate 26 below the first wash stop junction 51. Similarly, the connecting arm is located in the bottom of the middle plate below the second wash stop junction 52. Thus, a liquid interface is formed between the diluent and the blood sample at the wash stop junctions. As a result, a continuous fluidics circuit between the diluent in the reservoir 62 and the mixing chambers 48 and 49 is formed, causing diluent to wash out the remaining blood sample in the mixing chamber capillaries.

Because each mixing chamber 48 and 49 is positioned radially outward from the diluent reservoir 62, a centrifugal driving force is created by the centrifugal acceleration which causes flow of diluent from the diluent reservoir into the mixing chambers. The diluent reservoir drains through the diluent exit capillary 66, the diluent cross channel 70, and the diluent connecting channel 74. The diluent is forced through each wash stop junction 51 and 52, and washes out each mixing chamber inlet capillary 41 and 42. The diluent washes the reagent containing blood sample from the inlet capillaries into the mixing chambers.

Hence, the diluent flows from the crushed glass ampule 60 into diluent reservoir 62, through exit capillary 66, up the exit stop junction 68, through the cross channel 70 and down the cross channel exit capillary 72 to the diluent connecting channel 74. At that point in the assay process for multiple assays in the same cartridge, the flow of diluent is diverted into at least two different directions. The diluent flows into the first connecting arm 75 and into the second connecting arm 76. The diluent is forced up each wash stop junction 51 and 52 and into the mixing chamber inlet capillaries 41 and 42 to wash the remaining blood sample mixture down through the mixing chamber inlet capillaries 44 and 45 into the mixing chambers 48 and 49.

The diluent completely fills each mixing chamber 48 and 49 until the diluent fills the mixing chamber vents 80 and 81. While the mixing chambers are filling with diluent, air is being pushed out the vents, which perform as stop junctions. The two vents are sized small enough so that they withstand and prevent liquid flow out of the mixing chambers. There is insufficient pressure to overcome the capillary strength of the mixing chamber vents at this point and the diluent stops flowing once the sample and diluent mixture completely fills the mixing chambers.

Each mixing chamber 48 and 49 is filled with about two hundred seventy-five microliters of fluid, including eighty five microliters of blood sample and reagent previously added, fifteen microliters of blood sample from the inlet capillaries 41 and 42 and one hundred seventy-five microliters of diluent. Thus, at least a ten times wash out of the inlet capillaries is performed to remove all of the blood cells out of each inlet capillary and into the mixing chamber. The washout ratio of diluent to remaining blood sample is important to overcome any settling of the blood cells in the inlet capillaries.

At this point, the spinning of the cartridge 20 is stopped. It is important to recognize that each capillary, reservoir and stop junction is configured to permit the cartridge to resume a static state without the fluids further moving within the cartridge. Prior to analysis by the imaging instrument, the diluent, blood sample and reagent in the mixing chambers 48 and 49 must be thoroughly mixed. Preferably, each mixing chamber contains a mixing element which can be moved by a force external to the cartridge. For example, a magnet in the imaging instrument may be used to linearly reciprocate a ball or similar mixing element around the inside of the mixing chamber. Alternatively, the cartridge may be reciprocated to cause a ball to agitate the fluids within the mixing chamber.

The cartridge 20 and associated capillaries and stop junctions are configured to ensure that when the cartridge stops spinning, each of the fluid interfaces are maintained. The stop junctions prevent fluids from moving from one chamber or capillary to another, thus stabilizing the fluid positions once the cartridge is at rest. The strength of the stop junctions is in the range of 10–40 millimeters of water, more than sufficient to retain the diluent and sample in position. Once the sample, reagent and diluent are in the mixing chambers 48 and 49, the fluid mixture must be thoroughly blended. One method of mixing would be to mix all of the cartridges 20 in the imaging instrument at the same time. Concurrent mixing could be accomplished by reciprocating all of the cartridges at the same time. Another method of mixing the fluids in the mixing chambers is to index each cartridge to a fixed mixing station in the instrument. Sequential mixing requires that each cartridge is indexed to a different position for each mixing chamber in the cartridge.

Concurrent mixing of the fluids in the mixing chambers 48 and 49 may utilize the same reciprocating motion used early in the assay process dissolve the reagent in the application wells 35 and 36. To facilitate mixing, the mixing chambers walls are shaped with an angle so that when the cartridge 20 reciprocates back and forth a mixing ball 97 and 98 moves in a triangular motion within each mixing chamber. Thus, each mixing chamber of all the cartridges are mixing simultaneously. Concurrent mixing has some advantages over sequential mixing. For example, reciprocating the cartridge 20 eliminates undesirable magnetic forces that may be used in the sequential method. Likewise, the need for a magnetic mixing mechanism in the imaging instrument is eliminated. Similarly, the reciprocating mechanism is available since the cartridges are reciprocated in a previous step. Moreover, the mixing of all the cartridges is being performed simultaneously; therefore, there is no lag time from mixing the first mixing chamber 48 and 49 to mixing the last mixing chamber. One disadvantage of reciprocating the cartridges is that full length of the mixing chamber may not be swept by the mixing ball 97 and 98. Thus, a combination of concurrent and sequential mixing may be desirable.

The method for sequential mixing uses a permanent magnet moved in a linear motion in the imaging instrument and a magnetic stirrer in the mixing chambers 48 and 49 of each cartridge 20. The stirrer may be a metal or ceramic mixing ball 97 and 98, wand or similar mechanism, as is well known to those of ordinary skill in the art. The imaging instrument moves or indexes each cartridge so that the mixing chamber is located proximate the magnetic field, indexing one mixing chamber at a time. Each mixing ball is then reciprocated inside the chamber in the range of ten to twenty hertz for approximately two to ten seconds. The imaging instrument sequentially indexes to each cartridge until all mixing chambers are thoroughly blended.

One of the disadvantages of sequential mixing is the propensity of the components of the sample to settle. In particular, the cells in a blood sample could introduce error in the analysis of the sample. From the time the first mixing chamber 48 and 49 is mixed to the time the last mixing chamber is mixed, the sample in the first mixing chamber is allowed a significant amount of time to settle. In the disclosed configuration, the diluted sample is transferred out of each mixing chamber off the top of the tank. If significant settling has occurred, there will be a different (fewer) cells in the portion of the sample removed that which remains in the mixing chamber. Likewise, if the sample is drawn from near the bottom of the mixing chamber, the portion of the sample removed will have an undesirable high cell count. Thus, if any significant settling has occurred, error in the imaging analysis will be introduced from a non-homogeneous sample. To maintain a uniform distribution of sample within the mixing chambers, each mixing chamber is again indexed proximate the magnet in the imaging instrument and each mixing ball 97 and 98 is reciprocated for 0.2 to 1.0 seconds at two to ten hertz. This final mixing step is performed just prior to filling the scan capillaries 100 and 101.

After the sample, reagent and diluent are mixed, the cartridge 20 is subjected to a high speed spin to move a portion of the diluted sample into a pair of scan capillaries 100 and 101 for each assay. The cartridges are ramped up in ten seconds to one-hundred ten RPM, held at that speed for twenty seconds and then decelerated to zero RPM in five seconds. During the high speed spin, a portion of the mixed sample flows out of the mixing chambers 48 and 49 through mixing chamber vents 80 and 81, which otherwise perform as stop junctions. The high speed spin creates enough pressure at the vents to overcome the stop junction backpressure.

The diluted sample flows from the mixing chamber vents 80 and 81 through a pair of scan capillary connecting channels 84 and 85 in the top surface 27 of the middle plate 26 and the bottom surface 24 of the top plate 22. The diluted sample continues to flow through a pair of scan level transfer channels 86 and 87 in the bottom surface 28 of the middle plate. The pressure of the fluid moves the diluted sample through the transfer channels into a pair of scan capillary entry channels 88 and 89 and up through two scan capillary entry ports 90 and 91.

As shown in FIGS. 2 and 5, each scan capillary 100 and 101 is mounted in a pedestal 102 and 103 for each imaging analysis to be performed. The pedestals are mounted on the middle plate 26 and reside within pedestal cutouts 105 and 106 in the top plate 22. One end of each scan capillary is positioned proximate the scan capillary entry ports 90 and 91. The scan capillaries are open on one end for venting and connected to the entry ports on the other end. The diluted sample flows into each scan capillary by a combination of centrifugal forces, capillary forces and gravitational forces. The pressure at the scan capillary entry ports causes the scan capillary to fill from end to end. The increased pressure caused by the centrifugal acceleration of the fluid entering the scan capillary prevents bubble formation commonly seen when filling a scan capillary by capillary and gravitational forces alone. It has been observed that bubble formation is affected by the shape of the meniscus which is affected by the total prressure at the entrance to the scan capillary.

Each scan capillary 100 and 101 has outside dimensions of about 54.0 mm long by 0.255 mm high and about 0.870 mm wide. The inside cross-section of each scan capillary forms a rectangle about 0.1 mm by 0.666 mm, which creates very strong capillary forces. When the diluted sample reaches the end of the scan capillary, the strong capillary forces prevents the sample from flowing out of the distal end of the scan capillary. The diluted sample flows to a point where the diluent reservoir 62 is at about the same radial position as the diluent exit capillary 66 such that there is no or little centrifugal pressure on the fluid at the exit end of the scan capillary. Thus, there is little or no driving force for the diluted sample to be pushed out of the scan capillary once it is completely filled.

The scan capillaries 100 and 101 fill with about 275.0 microliters of the diluted sample. Of the 275.0 microliters of diluted sample blended in the application well 48 and 49, only 2.75 microliters is scanned by the imaging instrument to count cells. The internal cross-section of each scan capillary is preferably rectangular shaped to create a definite edge for the imaging instrument to detect. The scan capillaries are preferably made of high quality glass such as that sold under the trademark "PYREX 7740" from Corning Corp., of Corning N.Y., or under the trademark "DURAN 8330" from Schott Glass Technologies, Inc. of Duryea, Pa. Other suitable materials for the scan capillaries are acrylic, such as "Plexiglas VS-UVT" available from AltoHaas, North American Ltd. of Bristol, Pa. and polystyrenes, such as "Styron 663" available from the Dow Chemical Company of Midland, Mich.

The present invention includes an assay cartridge which includes the use of low centrifugal accelerations to dilute a whole blood sample. The use of low centrifugal accelerations to move the fluids within the cartridge has several advantages over using high spin rates and, thus, high centrifugal accelerations. Foremost, it is important that the blood components, such as target lymphocytes and red blood cells, do not depart significantly from their natural distribution within the sample. Whereas many prior art cartridge designs are specifically configured for cell separation, maintaining homogeneous cell or particle distribution within the sample heretofore has been of little or no concern in cartridge configuration. In the present invention, however, the fluidics circuit, i.e., the arrangement of the application wells, reservoirs, chambers, conduits and capillaries, are primarily configured to minimize cell migration and maintain a homogeneous distribution of particles in the sample. Additionally, the centrifugal accelerations applied to the cartridge are maintained at low values to allow for imaging instrument platters which are not dynamically balanced so as to minimize wear to the instrument. Similarly, the use of low centrifugal accelerations allows the use of stepper motors and cartridge registration techniques which would not be available if high centrifugal accelerations were utilized.

One of the underlying principles of the present invention is the use of capillary forces to move fluids without the use of an external force. A second underlying principle is that the flow of fluid through a capillary may be stopped by the creation of a stop junction or a stop flow capillary. In the present invention, a stop junction is configured in the cartridge by creating a sharp transition from a capillary of relatively small diameter to a conduit or chamber of relatively larger diameter. The surface tension of the fluid in the capillary creates a back pressure in the capillary which prevents flow. Each capillary forming a stop junction is configured such that the sum of capillary forces and gravitational forces alone will not overcome the capillary back pressure. A third principle used in the present invention is the use of low centrifugal accelerations to overcome the back pressure or to "break" the stop junction. A low centrifugal acceleration is applied to the cartridge, which creates a pressure in the liquid at the stop junction to induce flow through the stop junction.

Figure 12:
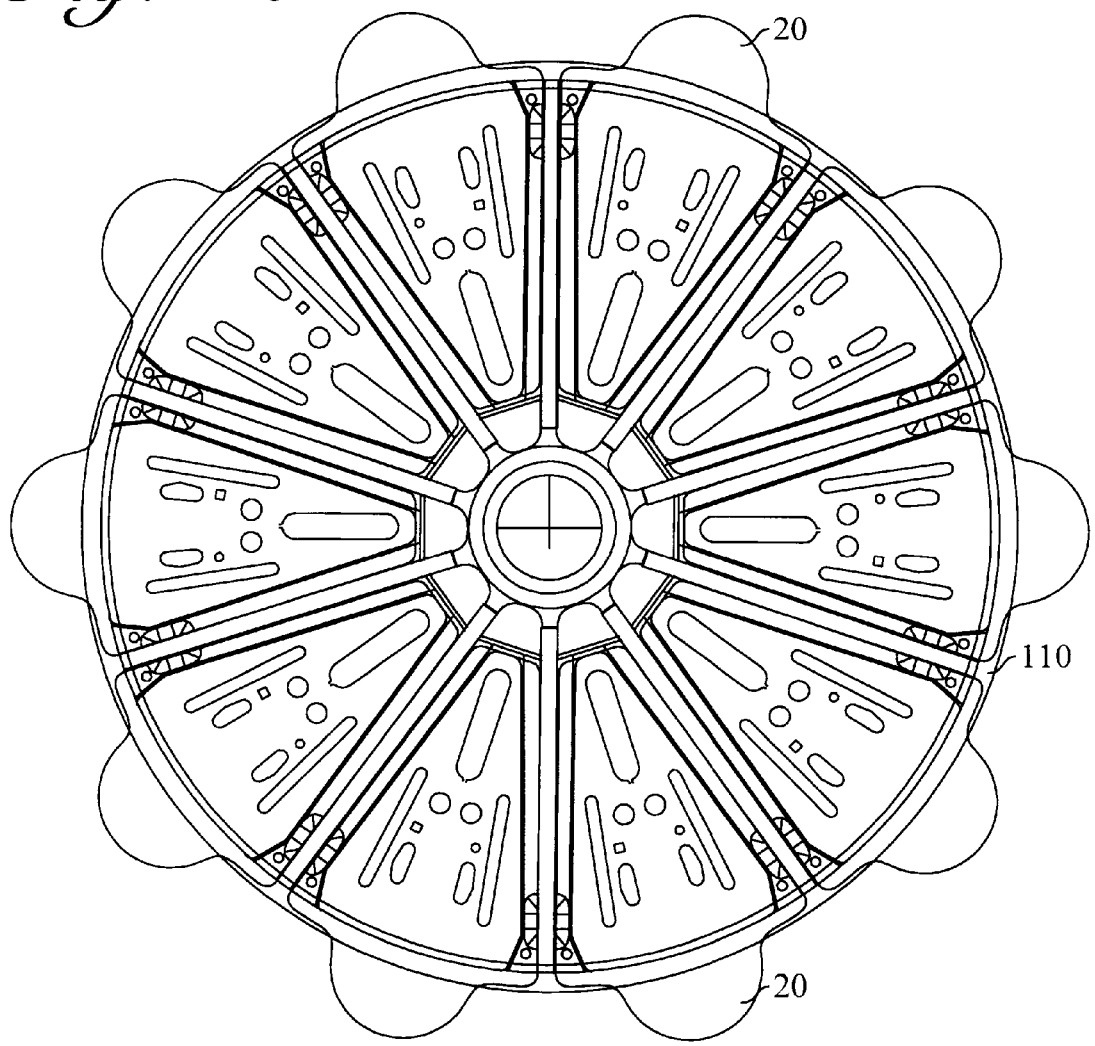
FIG. 12 is a top plan view of ten assay cartridges placed on a rotable platter of an imaging instrument.

In accordance with the invention, the centrifugal acceleration used to overcome the stop junction back pressure is relatively low in comparison to that found in prior art systems which spin an assay cartridge. Whereas prior art systems may spin a six inch diameter cartridge at 4000 RPM, one embodiment of the cartridge of the present invention is configured to be placed on a platter of about twelve inches in diameter and is spun at only 70 to 150 RPM. A twelve inch platter can accommodate ten cartridges as shown in FIG. 12. Other embodiments of fluidics circuits in a cartridge utilizing low centrifugal acceleration may be used to accommodate larger platters having more cartridges or smaller platters having fewer cartridges. For purposes of illustration, a six inch diameter platter spinning at 4000 RPM exerts a centrifugal acceleration of about 1300 g (12,750 m/sec$^2$) on the cartridge. Conversely, a twelve inch diameter platter spinning at 150 RPM will exert only about 2.5 g (24.5 m/sec$^2$) on the cartridge.

One of the reasons for maintaining a low centrifugal acceleration is to minimize the cell migration during the cartridge spin periods. As a rough estimate, a red blood cell will reach a terminal velocity in human plasma at about one micron per second when subjected to an acceleration equal to that of gravity at sea level. Since the imaging instrument is sensitive to particle or cell position, it is advantageous to minimize cell migration in the scan capillary, for example, limiting the particle migration to that of one thousand particle diameters.

It is also important to prevent the cells in the sample from migrating to a wall of the scan capillary where the cells will collect, prohibiting an accurate analysis of the sample. As is shown in FIG. 1, when the scan capillary is positioned longitudinally along the radius in the cartridge, a cell may migrate along a path that extends the full length of the capillary. If, however, the scan capillary is positioned substantially perpendicular to the radial axis of the platter, then the cells may only migrate along a comparatively short path before they encounter an edge of the scan capillary and accumulate along its wall.

There are several other reasons for desiring rotational speed of the imaging instrument platter and low centrifugal accelerations to be applied to the assay cartridge besides the problem of cell migration. For example, since the imaging instrument is designed to hold a variable number of cartridges on a platter as shown in FIG. 12, it is envisioned that instrument platter 110 often will be only partially loaded with cassettes. A platter loaded with an odd number of cassettes will not be dynamically balanced. Thus, high rotation speeds can subject the platter to forces that can damage the bearing surfaces of the imaging instrument. At low speeds such forces are greatly diminished, thereby improving the lifetime and reliability of the instrument.

Because a stepper motor system of the type envisioned to spin the imaging instrument platter has a limited dynamic range, it is advantageous to maintain low rotational speeds of the platter. For a given stepper motor system with a fixed number of steps per revolution and a maximum step rate there is always a trade off between the maximum rotational velocity attainable and the minimum step size or angular resolution of the system. If one desires to have a system with small angular change per step then it is important to design the system to have a low angular velocity given the limited dynamic range of the stepper motor. Therefore, the fluidics circuit of the cartridge is designed so as to operate at low angular velocity so as to enable using a platter that undergoes a small angular change per stepper motor step.

Similarly, as the angular velocity increases so does the centripetal forces on the cartridge. At high rotational speeds the forces can be great enough to require special fixturing to maintain accurate cartridge registration. Utilizing low rotational speeds maintains centrifugal forces at a low enough level to allow simple cartridge registration mechanics.

Thus, it is important when designing the cartridge of the present invention to calculate the minimum fluid pressure necessary to break a stop junction. Several variables are relevant to such a design. Foremost, as is taught in the prior art, the cross-sectional area of the stop flow capillary forming the stop junction is fundamental to creating the back pressure necessary to stop fluid flow for liquid used in the sample. Likewise, subjecting the cartridge to a high rotational speed or creating a gravitational head pressure to a fluid column is known in the art. The liquid surface tension and density are also factors contributing to the strength of the stop junction, but are normally treated as a constants, rather than design variables. Similarly, the contact angle between the capillary wall and the liquid is of concern, but absent some manufacturing treatment process, such as plasma etching of ABS, the contact angle may also be treated as a constant. It is part of the present invention that what was heretofore not recognized or taught in the art is to purposefully configure and select the radial position of the stop junction such that a "radial height" of a fluid column is manipulated to increase the pressure at the stop junction to initiate fluid flow, without subjecting the cartridge to unnecessarily high centrifugal accelerations.

The benefit of manipulation of the radial position of a stop junction relative to the most inward point of the fluid in a capillary can be recognized by review of certain basic engineering and physics equations outlined below. Such equations can be used to derive a specific relative radial position to the most inward position of a capillary necessary to overcome the capillary back pressure for a given stop junction cross-sectional area subjected to a desired centrifugal acceleration and rotational speed so as to effect a minimal or tolerable particle or cell migration. It is the difference in radial position between the most inward point of a fluid column and the radial position of the stop junction that determines the pressure that will be exerted at a stop junction for any given centrifugal acceleration.

Figure 14:
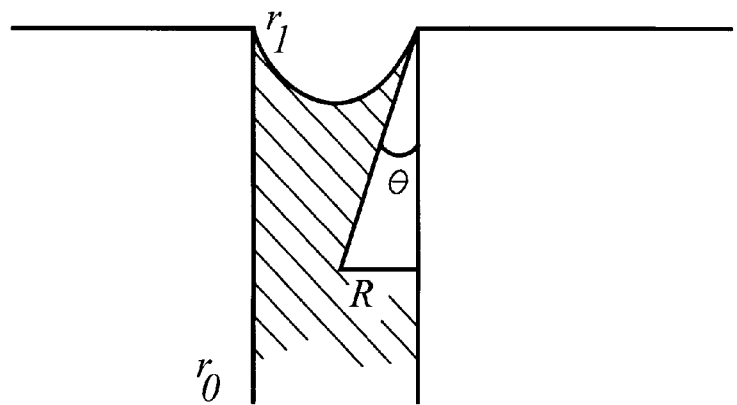
FIG. 14 is a schematic representation of a capillary forming a stop junction.

What follows herein is a discussion and derivation of the equations used to select radial positions of the components of the cartridge fluidics circuit. Some examples demonstrated and summarized in Table 1. For example, Equation 1 defines the pressure which must be generated to induce flow through a stop junction. Equation 1 is derived from an adaptation for capillary rise of the Young and Laplace equation, as outlined in The *Physical Chemistry of Surfaces*, Fourth Edition, by Arthur W. Adamson. As shown in FIG. 14, the radius, "R", of the capillary is the cross sectional radius of the capillary. Once the surface tension, "γ", of the fluid and the contact angle, "θ", between the fluid and capillary wall is known, the capillary back pressure, "$P_{cap}$", of the stop junction may be calculated.

$$P_{cap} = \frac{2\gamma \cos\theta}{R} \qquad \text{Equation 1}$$

$P_{cap}$ = capillary pressure $\gamma$ = surface tension of blood $\theta$ = contact angle of blood on cartridge $R$ = radius of stop junction Equations 2 through 5 derive the equation for centrifugal pressure, "$P_{cent}$". Equation 2 is the general equation relating the centrifugal pressure to density of the fluid, "$\rho$", the centrifugal acceleration applied to the fluid, "$a_{cent}$", and radial height of the fluid column, "$r_1 - r_0$". In deriving equation 2.1, the assumption is made that the fluid density is constant, since the fluid is essentially incompressible at the relevant pressures to which the fluid will be subjected.

$$P_{cent} = \int_{r_0}^{r_1} \rho a_{cent} dr \qquad \text{Equation 2}$$

$$P_{cent} = \rho \int_{r_0}^{r_1} a_{cent} dr \qquad \text{Equation 2.1}$$

In Equation 3, the centrifugal acceleration is expressed in terms of angular velocity of the imaging instrument platter, "$f$", and radial position of a segment of fluid measured from the center of the platter, "$r$". As shown in Equations 4 and 4.1, the formula for the centrifugal acceleration from Equation 3 may be substituted in Equation 2.1.

$$a_{cent} = 4\pi^2 f^2 r \qquad \text{Equation 3}$$

$$P_{cent} = 4\pi^2 \rho f^2 \int_{r_0}^{r_1} r dr \qquad \text{Equation 4}$$

$$P_{cent} = 4\pi^2 \rho f^2 \left( \frac{r_1^2}{2} - \frac{r_0^2}{2} \right) \qquad \text{Equation 4.1}$$

In deriving Equation 5, Equation 4 has been integrated (see Equation 4.1) and the centrifugal pressure is expressed in terms of the fluid density, the platter angular speed, the position of the inlet or most radially inward portion of the capillary or conduit, "$r_0$", and the radial position of the capillary outlet or of the stop junction, "$r_1$". Equation 5.1 is another version of Equation 5 where the relative contribution of the sum and difference of the radial terms can be seen. Thus, the pressure generated by the centrifugal acceleration, $P_{cent}$, to overcome the capillary back pressure may be directly affected by changing the radial height of the column of fluid ($r_1 + r_0$). Thus, the capillary back pressure may be overcome without merely changing the average radial position of the column, found in Equation 5.1 as the contribution ($r_1 - r_0$)/2, or the centrifugal acceleration applied to the cartridge, both of which adversely affect particle migration. This is a key principal not heretofore taught in the prior art.

$$P_{cent} = 2\pi^2 \rho f^2 (r_1^2 - r_0^2) \qquad \text{Equation 5}$$

$P_{cent}$ = centrifugal pressure $\rho$ = density of fluid $f$ = angular speed $r_1$ = radial position of outlet $r_2$ = radial position of inlet $$P_{cent} = 2\pi^2 \rho f^2 (r_1 + r_0)(r_1 - r_0) \qquad \text{Equation 5.1}$$

Equation 6 expresses the requirement that to cause flow through the stop junction the centrifugal pressure exerted on the fluid at the stop junction must exceed the capillary back pressure. In Equations 7 and 7.1, the Equation 5 and Equation 1 are substituted into Equation 6 for the centrifugal pressure and capillary back pressure. Equation 8 solves Equation 7 in terms of the angular speed required to cause flow through the stop junction.

$$P_{cent} > P_{cap} \qquad \text{Equation 6}$$

$$2\pi^2 \rho f^2 (r_1^2 - r_0^2) > \frac{2\gamma \cos\theta}{R} \qquad \text{Equation 7}$$

$$f^2 > \frac{\gamma \cos\theta}{\pi^2 \rho R (r_1^2 - r_0^2)} \qquad \text{Equation 7.1}$$

$$f > \sqrt{\frac{\gamma \cos\theta}{\pi^2 \rho R (r_1^2 - r_0^2)}} \qquad \text{Equation 8}$$

$f$ = angular speed required to break stop junction $\gamma$ = surface tension of blood $\theta$ = contact angle of blood on cartridge $\rho$ = density of blood $R$ = radius of stop junction $r_1$ = radial position of stop junction $r_0$ = radial position of sample or diluent inlet To verify that the centrifugal acceleration will provide minimal or tolerable cell migration, the radial velocity of a particle, "$v$", may be calculated. Equations 9 and 10 approximate the radial velocity of a particle when subjected to centrifugal acceleration. The equations are adaptations of Stoke's law, see *Perry's Chemical Engineers Handbook*, Equation 19–54. Referring to the constants in Table 1, the terminal velocity ($v_r$) of a red blood cell in plasma may be approximated using Equation 10. As part of the approximation, a sphere having a diameter of 6.4 microns ($D_p$) is used as the particle, since such a sphere has about the same volume as a red blood cell represented as a cylinder 4.3 microns in radius and 2.4 microns high. Using such values in Equation 10, the terminal velocity, or migration velocity, of a red blood cell is 1.56 microns per second.

$$v_r = \frac{a_{cent}(\rho_P - \rho)D_P^2}{18\mu} \qquad \text{Equation 9}$$

-continued $$v_r = \frac{4\pi^2 f^2 r(\rho_P - \rho)D_P^2}{18\mu}$$ Equation 10

$v_r$ = radial component of velocity of particle
$a_{acent}$ = centrifugal acceleration
$\rho_P$ = density of particle
$\rho$ = density of liquid phase
$D_p$ = diameter of spherical particle
$\mu$ = viscosity of liquid phase
$f$ = angular speed
$r$ = radial position of particle Table 1 is a summary of typical physical parameters, mechanical parameters, and sizing calculations. In the first box of the table, the fixed physical properties of the cartridge and fluid, e.g., the surface tension of blood and the contact angle of blood on plasma etched ABS, are listed. In the second box, design specific dimensions for the cartridge of the present invention are listed, including the radial position and diameter of the mixing chamber inlet stop junctions (SJ1), the diluent exit stop junction (SJ2) and the mixing chamber vents (SJ3). In the third box, the angular speed, the centrifugal acceleration and the centrifugal pressure at the three stop junctions are listed. These values are calculated using Equation 8, Equation 3, and Equation 5, respectively. Alternatively, if the desired centrifugal acceleration and centrifugal pressure are known, the radial position of the inlet ($r_0$) and outlet ($r_1$) may be selected by substitution of the appropriate values into Equations 1–10, e.g., Equation 5.1. The preferred range of the low level of centrifugal acceleration is from one to one hundred m/sec$^2$, and preferably about twenty m/sec$^2$. Similarly, the preferred range of radial height ($r_1-r_0$) is from one to one hundred fifty millimeters, and preferably about twenty-five millimeters.

While several particular forms of the invention have been illustrated and described, it will be apparent that various modifications can be made without departing from the spirit and scope of the invention. For example, references to materials of construction and specific dimensions are also not intended to be limiting in any manner and other materials and dimensions could be substituted and remain within the spirit and scope of the invention. Accordingly, it is not intended that the invention be limited, except as by the appended claims.

TABLE 1

| Fixed Physical Properties | |
|---|---|
| Surface Tension of Blood (N/m) γ | 0.056 |
| Contact Angle of Blood on Cartridge (degrees) θ | 35.0 |
| Density of Blood (kg/m$^3$) ρ | 1060.0 |
| Density of Plasma (kg/m$^3$) ρ | 1026.9 |
| Density of Red Blood cell (kg/m$^3$) $\rho_p$ | 1096.4 |
| Diameter of Red Blood cell (m) $D_p$ | 0.0000064 |
| Viscosity of Blood (kg/sec/m) μ | 0.00015 |
| Mechanical Parameters of Cartridge and Platter | |
| Radial Position of Sample Inlet (in) $r_0$ | 0.106 |

TABLE 1-continued

| Radial Position of Diluent Inlet (m) $r_0$ | 0.0927 | | |
|---|---|---|---|
| Stop Junction Number | SJ1 | SJ2 | SJ3 |
| Radial Position of Stop Junction (m) $r_1$ | 0.131 | 0.131 | 0.120 |
| Radius of Stop Junction (mm) R | 1.09 | 1.09 | 0.787 |
| Calculated Centrifugal Acceleration Required to Overcome Stop Junction | | | |
| Stop Junction Number | SJ1 | SJ2 | 5J3 |
| Angular Speed (RPM) $f$ | 69 | 58 | 114 |
| Centrifugal Pressure (mm H$_2$O) P$_{cent}$ | 17 | 17 | 24 |
| Centrifugal Acceleration (in/sec$^2$) a$_{cent}$ | 6.87 | 4.81 | 17.17 |

What is claimed is:

1. A cartridge for dilution of a whole blood sample, the cartridge comprising:
    a first receptacle configured to receive a whole blood sample;
    a first conduit in fluid communication with said first receptacle configured to move the whole blood sample from said first receptacle;
    a first fluid stop junction in fluid communication with said first conduit, said first fluid stop junction positioned radially outward from said first receptacle, said first fluid stop junction configured to prohibit the whole blood sample from flowing from said first conduit in the absence of centrifugal acceleration applied to the whole blood sample;
    a second receptacle in fluid communication with said first fluid stop junction, said second receptacle configured to receive the whole blood sample, wherein the sample flows from said first receptacle through said first conduit and said first fluid stop junction into said second receptacle upon application of a first low centrifugal acceleration to the whole blood sample in said first conduit, the low centrifugal acceleration having a range of 1 to 100 meters per second per second;
    a third receptacle;
    a second conduit in fluid communication with third receptacle, and configured to move diluent therefrom;
    a second fluid stop junction for connecting said second conduit to said first conduit, said second fluid stop junction configured to move diluent from said second conduit, wherein the diluent flows from said third receptacle through said second conduit and said second fluid stop junction into said first fluid conduit upon application of a second low centrifugal acceleration to the fluid in said second conduit and said second stop junction, the second low centrifugal acceleration having a range of 1 to 100 meters per second per second;
    retaining means for retaining a portion of the whole blood sample and diluent;
    a third stop junction in fluid communication with said second receptacle and in fluid communication with said retaining means.

2. The cartridge of claim 1, further comprising a mixing element residing in the second receptacle, the mixing element is configured to mix the whole blood sample and the diluent.

3. A method for moving a fluid sample in an assay cartridge, the method comprising the steps of:
    applying a fluid sample to a first application well;

providing a first capillary in fluid communication with the first application well and a first stop junction in fluid communication with a first reservoir, such that a first portion of the fluid sample moves into the first capillary and the first stop junction as a result of capillary forces, but does not move into the first reservoir; and applying a first low centrifugal acceleration to the fluid sample in the first capillary and in the first stop junction, the first low centrifugal acceleration having a range of 1 to 100 meters per second per second, thereby causing a second portion of the sample to move from the application well into the first reservoir.

4. The method of claim 3, further comprising the steps of:

providing a second reservoir, the second reservoir in fluid communication with a second capillary, the second capillary in fluid communication with a second stop junction, the second stop junction in fluid communication with the first reservoir, wherein the second reservoir contains diluent, a first portion of which moves into the second capillary and the second stop junction as a result of capillary forces, but does not move into the first reservoir; and applying a second low centrifugal acceleration to the diluent in the second capillary and in the second stop junction, the second low centrifugal acceleration having a range of 1 to 100 meters per second per second, thereby causing a second portion of the diluent to move from the second reservoir into the first reservoir.

5. The method of claim 4, further comprising the steps of:

providing a scan capillary in fluid communication with the first reservoir;

providing a third stop junction configured to prevent fluid flow from the first reservoir when the second low centrifugal acceleration is applied; and applying a third low centrifugal acceleration of greater magnitude than the second low centrifugal acceleration, the third low centrifugal acceleration having a range of 1 to 100 meters per second per second, such that the sample and diluent flow from the first reservoir into the scan capillary.

6. The method of claim 3, further comprising the step of measuring a predetermined amount of the fluid sample prior to and for use in performing said applying a fluid sample to a first application well step.

7. The method of claim 3, further comprising the step of measuring a predetermined amount of the sample prior to and for use in performing said applying a sample to a first application well step.

8. A method for diluting a sample in a cartridge, said method comprising the steps of:

applying a sample to a first application well;

providing a first capillary configured with a first stop junction in fluid communication with the application well;

applying a first low centrifugal acceleration to the sample and said application well, the first low centrifugal acceleration having a range of 1 to 100 meters per second per second, thereby causing the sample to move from the application well into a first reservoir connected to the first stop junction;

providing a second reservoir in fluid communication with a second capillary, the second capillary configured with a second stop junction in fluid communication with the first reservoir, wherein the second reservoir contains diluent; and applying a second low centrifugal acceleration to the second reservoir and second capillary, the second low centrifugal acceleration having a range of 1 to 100 meters per second per second, thereby causing the diluent to move from the second reservoir into the first reservoir.

9. The method of claim 8, further comprising the steps of:

providing a scan capillary in fluid communication with a third stop junction which prevents fluid flow from the first reservoir when the second low centrifugal force is applied; and applying a third low centrifugal acceleration to the sample and diluent in the first reservoir, the third low centrifugal acceleration being of greater magnitude than the second low centrifugal acceleration, said third low centrifugal acceleration having a range of 1 100 meters per second per second, such that the sample and diluent flow from said first reservoir into the scan capillary upon application of the third low centrifugal acceleration.

10. A method for making a stop junction for preventing fluid flow below a predetermined low centrifugal force and allowing fluid flow above the predetermined low centrifugal force, the method comprising the steps of:

selecting a fluid having a predetermined density and a predetermined surface tension;

providing a capillary in fluid communication with a reservoir at a junction forming a sharp transition, the capillary having a relatively small cross-sectional dimension immediately adjacent the junction and the reservoir having a relatively large cross-sectional dimension immediately adjacent the junction;

selecting a dimension and configuration for the cross-section of the capillary immediately adjacent the junction;

selecting a contact angle between the fluid in the capillary and the capillary wall;

selecting a low centrifugal acceleration to be applied to the fluid in the capillary; and selecting a most inwardly radial position and a most radial outward position of the fluid within the capillary such that prior to the application of the low centrifugal acceleration to the fluid in the capillary the fluid will not flow from the capillary to the reservoir, and application of the low centrifugal acceleration to the fluid in the capillary will causes the fluid to flow from the capillary to the reservoir, the low centrifugal acceleration having a range of 1 to 100 meters per second per second.

11. A method as in claim 10 wherein the step of selecting a dimension and configuration for the cross-section of the capillary at the junction comprises selecting a circular configuration.

12. A fluidics circuit which permits fluid flow at low centrifugal accelerations, the fluidics circuit comprising:

a capillary defining a fluid passage, said capillary having an inlet and an outlet spaced radially outward from the inlet by a radial distance;

a receptacle connected to the outlet a stop junction, wherein the radial distance is selected such that fluid will flow past the stop junction when a low centrifugal acceleration is applied to a column of fluid in the capillary, the low centrifugal acceleration having a range of 1 to 100 meters per second per second; and the column of fluid containing a suspended particle disposed between the inlet and the outlet and wherein the fluid passage of the capillary is configured so that the particle will not migrate a distance greater than one thousand times the diameter of the particle when a low centrifugal acceleration having a range of 1 to 100 meters per second per second is applied to the column of fluid in the capillary.

13. A method of diluting a sample of blood in a cartridge with a volume of diluent to a known volume, the method comprising the steps of:

providing an application well and a first capillary in fluid communication with the application well at a first end, and a mixing chamber at a second end;

providing a diluent reservoir, a second capillary in fluid communication with the diluent reservoir at the first end of said second capillary and connected proximate to the first end of the first capillary by a stop junction;

placing a known volume of a whole blood sample in the application well;

applying a first low centrifugal acceleration to the fluid in the application well to cause the fluid in the application well to pass through the first capillary into the mixing chamber, said first low centrifugal acceleration having a range of 1 to 100 meters per second per second;

releasing a volume of diluent in the diluent reservoir to cause the diluent to flow through the second capillary to the stop junction;

applying a second low centrifugal acceleration to the diluent to cause the diluent to flow past the stop junction through the first capillary into the mixing chamber, said second centrifugal acceleration having a range of 1 to 100 meters per second per second, wherein the amount of diluent that flows into the mixing chamber equals the volume of the mixing chamber less the known volume of whole blood.

14. The method of claim 13 comprising the additional steps of:

providing a releasable fluid container having diluent therein, the container being in the diluent reservoir, the container configured to release diluent in response to a stimulus;

applying a stimulus to release the diluent from the container.

15. The method of claim 14 wherein the stimulus is a crushing force.

16. A cartridge for processing a biological sample, said cartridge comprising:

an application well configured to receive the biological sample;

a first flow capillary, said first flow capillary having an inlet end and an outlet end, said inlet end in direct communication with said application well;

a mixing chamber, said first flow capillary extending between said application well and said mixing chamber, the outlet end of said first flow capillary in fluid communication with said mixing chamber;

a first stop junction proximal the outlet end of said first flow capillary, said first stop junction configured to prohibit the flow of the biological sample through said first stop junction in the absence of centrifugal acceleration applied to the sample in said application well and said first flow capillary, and further configured to permit the flow of the biological sample through said first stop junction upon the application of a first low centrifugal acceleration, to said application well and said first flow capillary; the first low centrifugal accelerator having a range of 1 to 100 meters per second per second to the biological sample;

a diluent reservoir configured to contain diluent fluid;

a second flow capillary, said second flow capillary in fluid communication with said diluent reservoir, and extending between said diluent reservoir and the inlet of said first flow capillary;

a second stop junction between said second flow capillary and the inlet of said first flow capillary, said second stop junction configured to prohibit the flow of diluent in the absence of centrifugal acceleration applied to said diluent and to permit the flow of the diluent fluid through said second stop junction upon the application of a second low centrifugal acceleration to the diluent fluid, the second low centrifugal acceleration having a range of 1 to 100 meters per second per second;

a scan capillary;

a third flow capillary, said third flow capillary being in fluid communication with said scan capillary and extending between said scan capillary and said mixing chamber;

a third stop junction located between said third flow capillary and said mixing chamber, said third stop junction configured to prohibit the flow of fluid from said mixing chamber to said third flow capillary in the absence of centrifugal acceleration applied to fluid, and to permit the flow of fluid through said third stop junction upon the application of a third low centrifugal acceleration to fluid in said mixing chamber, the third low centrifugal acceleration having a range of 1 to 100 meters per second per second.

\* \* \* \* \*